US011110191B2

(12) United States Patent
Katz

(10) Patent No.: US 11,110,191 B2
(45) Date of Patent: *Sep. 7, 2021

(54) METHOD AND SYSTEM FOR MONITORING ACTIVITY OF AN INDIVIDUAL

(71) Applicant: Antisep—Tech Ltd., LeHavim (IL)

(72) Inventor: Barak Katz, Ashkelon (IL)

(73) Assignee: Antisep—Tech Ltd., LeHavim (IL)

( * ) Notice: Subject to any disclaimer, the term of this patent is extended or adjusted under 35 U.S.C. 154(b) by 29 days.

This patent is subject to a terminal disclaimer.

(21) Appl. No.: 16/082,637

(22) PCT Filed: Jun. 1, 2016

(86) PCT No.: PCT/IL2016/050562
§ 371 (c)(1),
(2) Date: Sep. 6, 2018

(87) PCT Pub. No.: WO2016/193973
PCT Pub. Date: Dec. 8, 2016

(65) Prior Publication Data
US 2019/0117809 A1    Apr. 25, 2019

Related U.S. Application Data

(60) Provisional application No. 62/304,999, filed on Mar. 8, 2016.

(51) Int. Cl.
*G06T 7/50* (2017.01)
*G06K 9/00* (2006.01)
(Continued)

(52) U.S. Cl.
CPC .............. *A61L 2/24* (2013.01); *A61L 2/0047* (2013.01); *A61L 2/10* (2013.01); *B08B 7/0057* (2013.01);
(Continued)

(58) Field of Classification Search
CPC . A61L 2/24; A61L 2/0047; A61L 2/10; A61L 2202/11; A61L 2202/14;
(Continued)

(56) References Cited

U.S. PATENT DOCUMENTS 5,364,385 A    11/1994 Harms et al.
5,997,928 A    12/1999 Kaish et al.
(Continued)

FOREIGN PATENT DOCUMENTS

WO    WO 2011/123743    10/2011
WO    WO 2014/119804    8/2014
(Continued)

OTHER PUBLICATIONS

International Preliminary Report on Patentability dated Sep. 20, 2018 From the International Bureau of WIPO Re. Application No. PCT/IL2016/050562. (9 Pages).
(Continued)

*Primary Examiner* — Jacques M Saint Surin

(57) ABSTRACT

A monitoring system is disclosed. The monitoring system comprises a range detection system configured for scanning a scene to provide range data, the range data including data describing range to a marker that is detectable by the range detection system and that is placed on a hand of an individual in the scene; and a data processing system configured for processing the range data to identify the marker, to identify the hand based, at least in part on the range to the marker, and to monitor hygienic activity of an individual in the scene.

19 Claims, 12 Drawing Sheets

(51) Int. Cl.
*B08B 7/00* (2006.01)
*A61L 2/00* (2006.01)
*A61L 2/10* (2006.01)
*G06K 9/20* (2006.01)
*A61L 2/24* (2006.01)

(52) U.S. Cl.
CPC ..... *G06K 9/00201* (2013.01); *G06K 9/00771* (2013.01); *G06K 9/2063* (2013.01); *G06T 7/50* (2017.01); *A61L 2202/11* (2013.01); *A61L 2202/14* (2013.01); *G06T 2207/10028* (2013.01); *G06T 2207/30004* (2013.01); *G06T 2207/30196* (2013.01); *G06T 2207/30204* (2013.01)

(58) Field of Classification Search
CPC ............ G06T 7/50; G06T 2207/10028; G06T 2207/30204; G06T 2207/30196; G06T 2207/30004; G06K 9/00771; G06K 9/00201; G06K 9/2063; B08B 7/0057
USPC ...................................................... 340/539.12
See application file for complete search history.

(56) References Cited

U.S. PATENT DOCUMENTS

| | | | |
|---|---|---|---|
| 7,502,643 B2 | 3/2009 | Farringdon et al. | |
| 8,320,612 B2 | 11/2012 | Knobel et al. | |
| 8,395,515 B2 | 3/2013 | Tokhtuev et al. | |
| 8,698,637 B2 * | 4/2014 | Raichman | G08B 21/245 340/573.1 |
| 8,760,295 B2 | 6/2014 | Forster | |
| 9,641,808 B2 | 5/2017 | Rose et al. | |
| 10,754,924 B2 * | 8/2020 | Katz | G06F 19/325 |
| 2003/0065523 A1 | 4/2003 | Pruche et al. | |
| 2003/0120183 A1 | 6/2003 | Simmons | |
| 2005/0202844 A1 | 9/2005 | Jabri et al. | |
| 2007/0086911 A1 | 4/2007 | Yamazaki et al. | |
| 2008/0085228 A1 | 4/2008 | Yamazaki et al. | |
| 2008/0162352 A1 | 7/2008 | Gizewski | |
| 2009/0005650 A1 | 1/2009 | Angell et al. | |
| 2009/0068620 A1 | 3/2009 | Knobel et al. | |
| 2009/0091458 A1 * | 4/2009 | Deutsch | G06Q 50/22 340/573.1 |
| 2010/0081921 A1 | 4/2010 | Urban et al. | |
| 2010/0153374 A1 | 6/2010 | LeBlond et al. | |
| 2011/0227740 A1 | 9/2011 | Wohltjen | |
| 2011/0254682 A1 | 10/2011 | Sigrist Christensen | |
| 2011/0301441 A1 | 12/2011 | Bandic et al. | |
| 2012/0002066 A1 | 1/2012 | Wang | |
| 2012/0112883 A1 | 5/2012 | Wallace et al. | |
| 2012/0212344 A1 * | 8/2012 | Forsberg | G08B 3/10 340/573.1 |
| 2012/0212582 A1 | 8/2012 | Deutsch | |
| 2012/0253241 A1 | 10/2012 | Levital et al. | |
| 2013/0011931 A1 | 5/2013 | Alper | |
| 2013/0122807 A1 | 5/2013 | Tenarvitz et al. | |
| 2013/0270459 A1 | 10/2013 | Fontani | |
| 2014/0060104 A1 | 3/2014 | Shur et al. | |
| 2014/0070950 A1 | 3/2014 | Snodgrass | |
| 2014/0169622 A1 | 6/2014 | Dryer et al. | |
| 2014/0266692 A1 * | 9/2014 | Freedman | G08B 21/245 340/539.11 |
| 2015/0022361 A1 | 1/2015 | Gaisser et al. | |
| 2015/0170501 A1 | 6/2015 | Mukherji et al. | |
| 2016/0062469 A1 | 3/2016 | Abi-Rached et al. | |
| 2017/0076042 A1 | 3/2017 | Katz et al. | |

FOREIGN PATENT DOCUMENTS

| | | |
|---|---|---|
| WO | WO 2015/087331 | 6/2015 |
| WO | WO 2016/193973 | 12/2016 |

OTHER PUBLICATIONS

International Preliminary Report on Patentability dated Jun. 23, 2016 From the International Bureau of WIPO Re. Application No. PCT/IL2014/051084.
International Search Report and the Written Opinion dated Sep. 19, 2016 From the International Searching Authority Re. Application No. PCT/IL2016/050562.
International Search Report and the Written Opinion dated Apr. 30, 2015 From the International Searching Authority Re. Application No. PCT/IL2014/051084.
Invitation to Pay Additional Fees Dated Feb. 20, 2015 From the International Searching Authority Re. Application No. PCT/IL2014/051084.
Official Action dated May 23, 2018 From the U.S. Patent and Trademark Office U.S. Appl. No. 15/102,929. (36 pages).
Official Action dated Aug. 31, 2017 From the U.S. Patent and Trademark Office U.S. Appl. No. 15/102,929. (28 pages).
Supplementary European Search Report and the European Search Opinion dated Aug. 8, 2017 From the European Patent Office Re. Application No. 14868767.6. (12 Pages).
Chen et al. "Using Computer Vision and Depth Sensing to Measure Healthcare Worker-Patient Contacts and Personal Protective Equipment Adherence Within Hospital Rooms", Open Forum Infectious Diseases, 3(1): ofv200-1-ofv200-6, Published Online Dec. 28, 2015.
Chen et al. "Using Computer Vision and Depth Sensing to Measure Healthcare Worker-Patient Contacts and Personal Protective Equipment Adherence Within Hospital Rooms", University of Iowa, Computational Epidemiology Research, Poster, 2014.
Official Action dated Dec. 20, 2018 From the U.S. Patent and Trademark Office U.S. Appl. No. 15/102,929. (38 pages).
Notice of Allowance dated Apr. 23, 2020 from the U.S. Patent and Trademark Office U.S. Appl. No. 15/102,929. (32 pages).

* cited by examiner

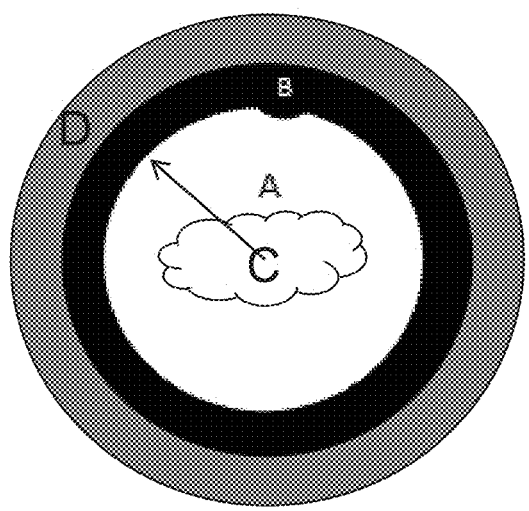 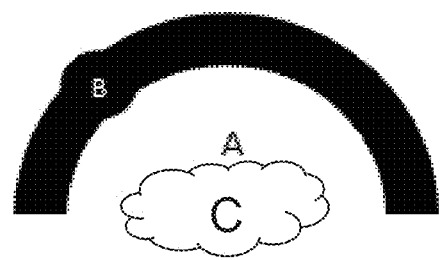
FIG. 10A                    FIG. 10B

METHOD AND SYSTEM FOR MONITORING ACTIVITY OF AN INDIVIDUAL

RELATED APPLICATIONS

This application is a National Phase of PCT Patent Application No. PCT/IL2016/050562 having International filing date of Jun. 1, 2016, which claims the benefit of priority under 35 USC § 119(e) of U.S. Provisional Patent Application Nos. 62/304,999 filed on Mar. 8, 2016. The contents of the above applications are all incorporated by reference as if fully set forth herein in their entirety.

FIELD AND BACKGROUND OF THE INVENTION

The present invention, in some embodiments thereof, relates to monitoring and, more particularly, but not exclusively, to a method and system for monitoring activity, e.g., hygienic activity of an individual.

Individuals in need of medical attention for a variety of ailments or conditions typically seek clinical treatment from a healthcare provider, nursing homes etc. Such treatment may include a combination of procedures, medications or other therapies to stabilize and/or improve the health of an individual or patient. However, the process of providing clinical treatment brings with it the risk of side effects. One such side effect of significant concern when patients seek procedure-related treatments from a healthcare provider is infections.

Substantial literature exists on infections, including nosocomial infections, which are prevalent in all patient care facilities including hospitals and nursing homes. These infections pose a significant health risk to hospitalized patients by delaying healing, extending the length of hospitalization and increasing the human and financial cost of care. Research reveals that several types of microorganisms can be transferred by hand to live hosts, thereby producing nosocomial infections.

Whether resulting from clinical issues such as contaminated equipment, individual patient health conditions, or other factors, infections can have a serious impact on the stability of a patient's health status and affect their ability to recover from a health condition. As a result, infections related to healthcare treatment delivery represent an increased risk to public health, and create a significant clinical and financial burden to society.

Moreover, due to economic pressure from health care reforms paired and a steady increase in demand for hospital services, hospitals are forced to do more with less. This places emphasis on controlling infection rates which are known to be a major reason for increment of hospitalization length of stay (LOS) and patient readmissions.

U.S. Published Application No. 20100073162 discloses a method for ensuring hand hygiene compliance. The method comprises the steps of sensing whether a person has washed their hands, determining a hand wash state of the person's hands, indicating the hand wash state of the person's hands; and alerting an individual of the hand wash state of the person's hands.

International Patent Application, Publication No. WO2015/087331, the contents of which are hereby incorporated by reference, describes a monitoring system that comprises a range detection system for scanning a scene to provide range data, and a data processing system for processing the range data to monitor hygienic activity of an individual in the scene.

Additional background art includes U.S. Published Application Nos. 20130122807, 20120112883, 2013011931, and 20130270459, the contents of which are hereby incorporated by reference.

SUMMARY OF THE INVENTION

According to an aspect of some embodiments of the present invention there is provided a monitoring system. The system comprises a range detection system configured for scanning a scene to provide range data arranged gridwise over a plurality of picture elements, the range data including data describing range to a marker that is detectable by the range detection system and that is placed on a hand of an individual in the scene; and a data processing system configured for processing the range data to identify the marker, to identify the hand based, at least in part on the range to the marker, and to monitor hygienic activity of an individual in the scene.

According to some embodiments of the invention the range detection system scans the scene from a single view point.

According to some embodiments of the invention the picture elements are devoid of any color data and any grayscale data.

According to some embodiments of the invention the range detection system provides range imaging data, and the data processing system is configured for removing from each picture-element any color data or grayscale data that allow identifying any individual in the scene.

According to some embodiments of the invention the data processing system is configured to identify a medical treatment device in the scene, and contact events between the individual and the medical treatment device, and to determine a time window encompassing both the hygienic activity and the contact events.

According to some embodiments of the invention the data processing system is configured to identify contact events between the individual and an organ of a patient in the scene, and to issue a notification when the contact events are not preceded or not followed by the hygienic activity.

According to some embodiments of the invention the system comprises an electromagnetic signaling system configured to project a light beam on the individual or an object in the scene based on the hygienic activity or lack thereof.

According to some embodiments of the invention the data processing system is configured to identify points of contact between the individual and objects in the scene, wherein the system comprises an electromagnetic disinfecting system configured to project a disinfecting light beam on at least one of the points of contact.

According to an aspect of some embodiments of the present invention there is provided a method of monitoring. The method comprises: scanning a scene to provide range data to a marker that is placed on a hand of an individual in the scene; and processing the range data to identify the hand based, at least in part on the range to the marker, and to monitor hygienic activity of an individual in the scene.

According to some embodiments of the invention the scanning is from a single view point.

According to some embodiments the method comprises identifying a medical treatment device in the scene and contact events between the individual and the medical treatment device, and determining a time window encompassing both the hygienic activity and the contact events.

According to some embodiments the method comprises identifying contact events between the individual and an organ of a patient in the scene, and issuing a notification when the contact events are not preceded or not followed by the hygienic activity.

According to some embodiments the method comprises projecting a light beam on the individual or an object in the scene based on the hygienic activity or lack thereof.

According to some embodiments the method comprises identifying points of contact between the individual and objects in the scene, and projecting a disinfecting light beam on at least one of the points of contact.

According to an aspect of some embodiments of the present invention there is provided a method of monitoring. The method comprises: scanning a scene and provide range data including data describing a range to a hand of an individual in the scene and data describing a location of the individual within the scene; and correction the data describing the range to the hand based, at least in part on the data describing the location of the individual within the scene.

According to some embodiments of the invention the method comprises processing the corrected data to monitor hygienic activity of an individual in the scene.

According to some embodiments the method comprises determining at least one of a posture and an orientation of the individual, wherein the correction is based, at least in part, on at least one of the posture and orientation.

According to some embodiments the method comprises identifying contact events between the individual and an organ of a patient in the scene, and issuing a notification when the contact events are not preceded or not followed by the hygienic activity.

According to some embodiments the method comprises projecting a light beam on the individual or an object in the scene based on the hygienic activity or lack thereof.

According to some embodiments the method comprises identifying points of contact between the individual and objects in the scene, and projecting a disinfecting light beam on at least one of the points of contact.

According to an aspect of some embodiments of the present invention there is provided a disinfection system. The disinfection system comprises: a range detection system configured for scanning a scene to provide range data arranged gridwise over a plurality of picture elements; a data processing system configured for processing the range data to identify an object in the scene; and an irradiation system communicating with the data processing system and configured for directing a focused disinfecting radiation onto the identified object.

According to some embodiments of the invention the identification is by a marker placed on the object.

According to some embodiments of the invention the data processing system is configured to obtain contamination status of the object, and wherein the irradiation system is configured to direct the focused disinfecting radiation responsively to the contamination status.

According to some embodiments of the invention the data processing system is configured to identify contact event between an individual in the scene and the object and to determine the contamination status based, at least in part, on the contact event.

According to some embodiments of the invention the data processing system is configured to identify hygienic activity or lack of hygienic activity of the individual prior to the contact event and to determine the contamination status based, at least in part, on the identification of hygienic activity or lack thereof.

According to some embodiments of the invention the object comprises a medical device.

According to some embodiments of the invention the object comprises a medical device.

According to some embodiments of the invention the object comprises a wound of a patient.

According to some embodiments of the invention the object comprises a wound of a patient.

According to some embodiments of the invention the system comprises the wound dressing.

According to some embodiments of the invention the wound dressing comprises a first region that is transmissive to the radiation and a second region that is non-transmissive to the radiation.

According to some embodiments of the invention the wound dressing comprises a first region that is transmissive to the radiation and a second region that is detectable by the range detection system and identifiable by the data processing system, the first region and the second region occupying different areas of the wound dressing.

According to some embodiments of the invention the wound dressing comprises a first region that is transmissive to the radiation, a second region that is detectable by the range detection system and identifiable by the data processing system, and a third region that is non-transmissive to the radiation, and wherein at least two of the first, the second and the third regions occupy different areas of the wound dressing.

According to an aspect of some embodiments of the present invention there is provided a method of disinfection. The method comprises: scanning a scene to provide range data describing the scene; processing the range data to identify an object in the scene; and directing a focused disinfecting radiation onto the identified object.

According to some embodiments of the invention the identification comprises identifying a marker placed on the object.

According to some embodiments of the invention the method comprises obtaining contamination status of the object, wherein the directing the focused disinfecting radiation is responsively to the contamination status.

According to some embodiments of the invention the obtaining the contamination status comprises identifying contact event between an individual in the scene and the object and to determining the contamination status based, at least in part, on the contact event.

According to some embodiments of the invention the method comprises identifying hygienic activity or lack of hygienic activity of the individual prior to the contact event, wherein the determining the contamination status based, at least in part, on the identification of hygienic activity or lack thereof.

According to some embodiments of the invention the object comprises a medical device.

According to some embodiments of the invention the object comprises a wound of a patient.

According to some embodiments of the invention the wound is dressed with a wound dressing being detectable by the range detection system and identifiable by the data processing system.

According to an aspect of some embodiments of the present invention there is provided a wound dressing assembly. The wound dressing assembly comprises a first region being transmissive to a disinfecting radiation, and a second region having a marker being identifiable by a range detection system, the first region and the second region occupying different areas of the wound dressing.

According to some embodiments of the invention the wound dressing assembly comprises a third region that is non-transmissive to the radiation.

According to some embodiments of the invention the second region at least partially surrounds the first region.

According to some embodiments of the invention the second region at least partially surrounds the first region, and the third region at least partially surrounds the second region.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 10A and 10B are schematic illustrations of a wound dressing according to some embodiments of the present invention.

DESCRIPTION OF SPECIFIC EMBODIMENTS OF THE INVENTION

Figure 1:
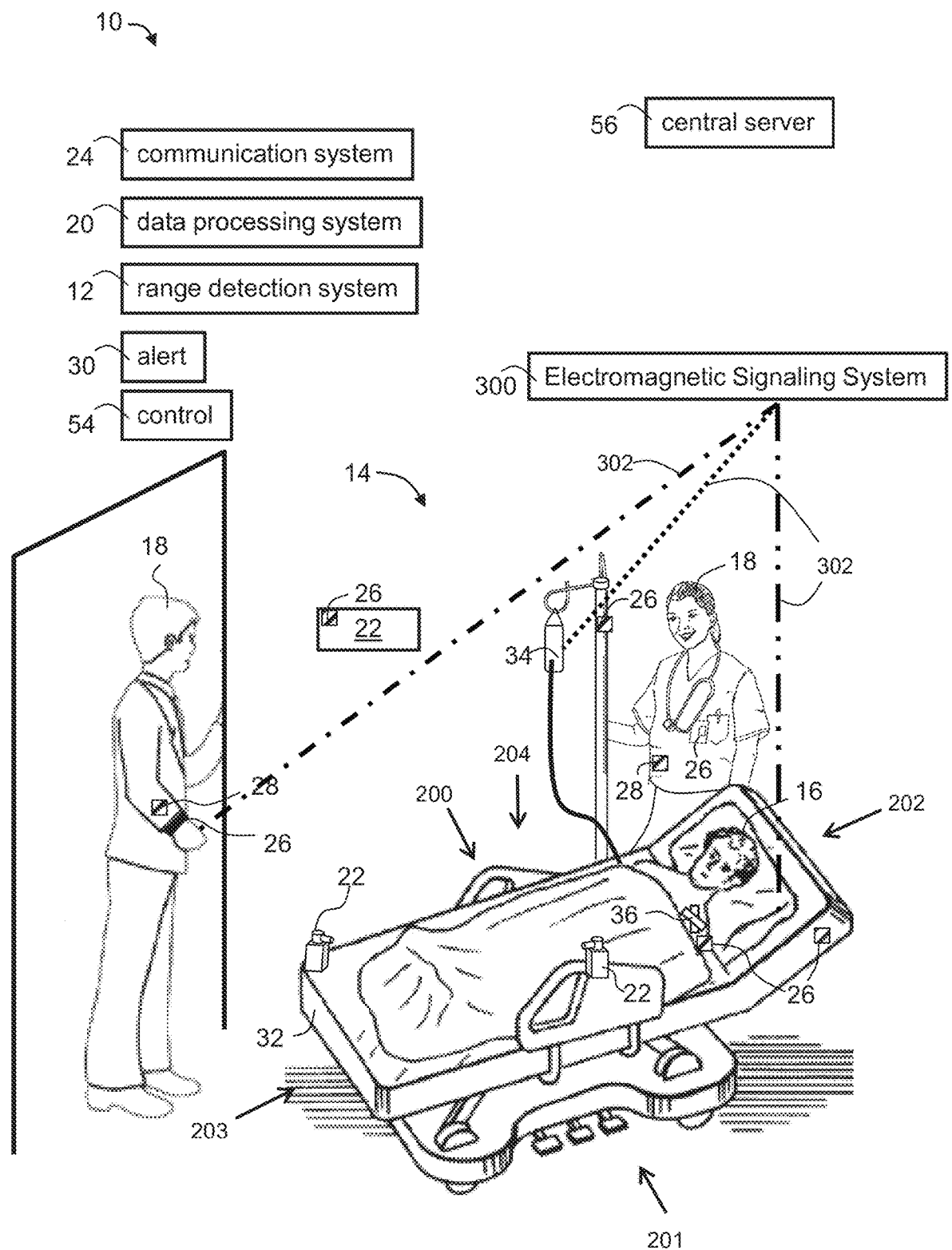
FIG. 1 is a schematic illustration of a monitoring system, according to some embodiments of the present invention.

The present invention, in some embodiments thereof, relates to monitoring and, more particularly, but not exclusively, to a method and system for monitoring activity, e.g., hygienic activity of an individual.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Computer programs implementing the technique of the present embodiments can commonly be distributed to users on a distribution medium such as, but not limited to, a floppy disk, a CD-ROM, a flash memory device and a portable hard drive. From the distribution medium, the computer programs can be copied to a hard disk or a similar intermediate storage medium. The computer programs can be run by loading the computer instructions either from their distribution medium or their intermediate storage medium into the execution memory of the computer, configuring the computer to act in accordance with the method of this invention. All these operations are well-known to those skilled in the art of computer systems.

The technique of some embodiments of the present invention can be embodied in many forms. For example, it can be embodied in on a tangible medium such as a computer for performing the method operations. It can be embodied on a computer readable medium, comprising non-volatile computer readable instructions for carrying out the method operations. In can also be embodied in electronic device having digital computer capabilities arranged to run the computer program on the tangible medium or execute the instruction on a computer readable medium.

Referring now to the drawings, FIG. 1 is a schematic illustration of a monitoring system 10, according to some embodiments of the present invention. System 10 optionally and preferably includes a range detection system 12 configured for scanning a scene 14 and provide range data corresponding to the scene. Scene 14 is preferably a medical environment, such as, but not limited to, a hospital room, a intensive care units, neonatal intensive care units, nursing homes, ambulatory care clinics, dialysis units, cardiac catheterization units, surgical suites, isolations rooms, burn centers, skin grafting centers or the like. The environment 14 is typically occupied by a patient 16, and one or more individuals 18 such as a medical practitioner or a guest. Other objects and devices may also be present in environment 14. For example, the environment 14 may be occupied with multiple devices or systems that individual 18 interacts with or respond to. When environment 14 is a medical environment, e.g., a hospital room, these objects may include at least one of: a medical device 34 positioned nearby patient 16, a medical device 36 in contact with patient 16, a hand cleansing device 22 (either wall-mounted or mobile), a support structure 32 and the like. In the schematic illustration of FIG. 1, which is not to be considered as limiting, medical device 34 is shown as an infusion bag, medical device 36 is shown as an attachable patch, and support structure 32 is shown as a hospital bed, but other types of medical devices, support structures, as well as other objects are also contemplated.

A non-exhaustive list of objects that may be present in environment 14 includes, a audiometer, a sterilizer, a bed pan, a urinal, a blood drawing chair, a blood pressure monitor, a bowl, a basin, a bucket, a cabinet, a cart, a casting equipment, a catheter tray, a centrifuge, a chair, a cholesterol monitor, a colposcope, a containment system, a couches, a recovery crib, a cryosurgical equipment, a defibrillator, a diagnostic station, a dispenser, an ECG monitor, ECG electrodes, electrosurgery accessories, an electrosurgery generator, a endoscope, an endoscopy video system, a exam table, a fetal monitor, a furniture, a medical gel warmer, a glucose monitor, a hamper, a height rod, a hemoglobin test, a holter monitor, a illuminator, an infantometer, a INR testing instrument stand, a instrument table, a instrument tray, a instrument, a IV pole, a jar, a cup, a laryngoscope, a lift, a lighting mattresses, an overbed table, a patient monitor, a patient positioning equipment, a phlebotomy cabinet, a pinwheel, a pressure infusion bag, a privacy screen, a pulse oximeter, a recliner, a reflex hammer, a refrigerator, a freezer, a respiratory analyzer, a restraint board, a room signal flag, a scale, a sharps container, a smoke evacuator, a sink, a suction device, a spirometer, a stadiometer, a step stool, a sterilization tray, a sterilization basket, a stethoscope, a stool, a stress test, a thermometer, a transport chair, a transport stretcher, a trapeze, a trash can, a treadmill, a ultrasound device, a vital signs monitor, a wall desk, a wall socket, a warmer, a water distiller and a wheelchair.

The range data provided by system 12 are arranged gridwise over a plurality of picture elements (e.g., pixels). Preferably, but not necessarily, the picture elements are devoid of any color data and any grayscale data, so as to protect the visual privacy of patient 16 and/or individual 18.

Range detection system 12 can employ any known range detection technique, including active illumination technique and passive techniques. Active illumination techniques suitable for the present embodiments including, without limitation, laser strip techniques [A. Clark, M. Wallace, and G. L. Pronzato, "Measuring range using a triangulation sensor with variable geometry," IEEE Trans. Rob. Autom. 14, 60-68 (1998)], laser propagation time techniques [M. D. Adams, "Lidar Design, Use and Calibration Concepts for Correct Environmental Detection", IEEE Transactions on Robotics and Automation, Vol 16(6), December 2000], time-of-light (ToF) sensing techniques [A. Kolb, E. Barth and R. Koch: "ToF-Sensors: New Dimensions for Realism and Interactivity," Proc. IEEE Comp. Soc. Conf. on Computer Vision and Pattern Recognition (CVPR), 1518-1523 (2008)], profile from focus techniques [A. M. Loh and P. D. Kovesi, "Estimation of surface normal of a curved surface using texture," In Proc. of the 7th Australian Pattern Recognition Society Conference—Digital Image Computing: Techniques and Applications, 155-164 (2003)], and structured light techniques [David Catuhe "Programming with the Kinect for Windows Software Development Kit, Add gesture and posture recognition to your applications", Microsoft Press].

Also contemplated are depth from motion techniques [R. C. Bolles, H. H. Baker, D. H. Marimont, "Epipolar-plane image analysis: An approach to determining structure from motion," International Journal of Computer Vision 1(1): 7-55 (1987)], stereoscopic techniques [E. Trucco, A. Verri, "Introductory techniques for 3D computer vision," Prentice Hall, 140-143 (1998)].

Additionally contemplated are the techniques disclosed in Irshad Ali, 2009, "Detection and Tracking of Multiple Humans in High-Density Crowds," Thesis, Department of Computer Science Engineering, Asian Institute of Technology School of Engineering and Technology, Thailand; Bo Wu and Nevatia R., Detection of Multiple Partially Occluded Humans in a Single Image by Bayesian Combination of Edgelet Part Detectors, In 10th IEEE International Conference on Computer Vision, ICCV'05, Volume 1, Pages 90-97, 2005; Saad M. Khan and Mubarak Shah, A Multiview Approach to Tracking People in Crowded Scenes using a Planar Homography Constraint, In IEEE International Conference on Computer Vision, ECCV'06, Volume 3954, Pages 133-146, 2006; Cheriyadat, A. M., Bhaduri B. L. and Radke R. J., Detecting multiple moving objects in crowded environments with coherent motion regions, in IEEE Computer Society Conference, Pages: 1-8, 2008; and Marchand E., Bouthemy P., Chaumette F. and Moreau V., Robust real-time visual tracking using a 2D-3D model-based approach. In Proc. Of the 7th IEEE International Conference on Computer Vision, ICCV'99, Volume 1, Pages 262-268, Kerkira, Greece, September 1999; C. Regazzoni, A. Cavallaro, Y. Wu, J. Konrad, A. Hampapur, Video Analytics for Surveillance: Theory and Practice, IEEE Signal Processing Magazine, September 2010; Fisher, J. 2003. "A Line Calling System to Improve Line Umpire Performance." In, ed. Stuart Miller. International Tennis Federation; Kai-Che Liu, Fu-Chiang Jan, Wen-Chao Chen, Cheng-Feng Wu, Tsu-Han Chen, Qi Wu, "Example-Based Two-Dimensional to Three-Dimensional Image Conversion Method, Computer Readable Medium Therefore, and System", U.S. Published Application No. 2010014781; Chien-Hung, Chen, Chun-Chieh Chiu and Yue-Li Chao, "Method for generating 3D image", U.S. Published Application No. 2011090318; and Barak Katz and Oded Zahavi, method and system for extracting three-dimensional information, International Publication No. WO2012029058, the contents of which are hereby incorporated by reference.

Range detection system 12 can also employ other technologies, optionally and preferably in combination with the above techniques, which technologies include, but are not limited to, WiFi location technology, Bluetooth, Ultra wideband and RF tagging technologies, and sensor technologies such as, but not limited to, accelerometers and gyroscopes.

Volume sensors can also be employed, for example, for determining presence of individuals in areas without imaging coverage.

Also contemplated are commercially available depth sensors, such as, but not limited to, DepthSense® 311 by Softkinetic Ltd., and SR4000 or SR4500 by MESA Imaging Ltd.

In various exemplary embodiments of the invention range detection system 12 employs active infrared illumination technique for generating the range data. In some embodiments of the present invention system 12 is or comprises a structured illumination Kinect camera such as the camera installed in the commercial Xbox™ and Xbox 360™ systems, and/or TOF camera such as the camera installed in the commercial Xbox One™ system, all of which are marketed by Microsoft Corporation.

In some embodiments of the present invention system 12 comprises two or more range detection systems that operate according to different principles. For example, system 12 can include a structured illumination system and a TOF system that are viewing the environment simultaneously. The advantage of these embodiments is that they reducing light ambiguity among different sensors.

When system 12 comprises a camera that can provide range data as well as color or grayscale data, the color or grayscale sensors in the camera are optionally blocked so as to prevent the camera from providing any color data and any grayscale data. The camera can comprise a diffuser element placed in front of the color sensors, in which case it is not necessary to prevent the camera from providing color data. The diffuser element is preferably configured to sufficiently blur color image provided by the camera so as to prevent identification of individual 18 and/or patient 16. The advantage of these embodiments is that it increases the amount of information collected by system 12 without compromising the privacy of the individuals in the environment.

System 10 optionally and preferably comprises a data processing system 20, more preferably an image processor, configured for processing the range data provided by system 10. System 20 can be dedicated circuitry or, in some embodiments, a general purpose computer, configured for receiving the range data, and executing at least some of the operations described herein. When range detection system 12 provides range imaging data, data processing system 20 optionally removes from each picture-element of the data any color data or grayscale data.

Thus, the present embodiments contemplate processing of a plurality of picture elements wherein each picture-element stores a range value, but does not store light intensity value, neither in the form of a grayscale value nor in the form of a plurality of intensity values corresponding to a respective plurality of colors (e.g., a plurality of RGB values). Such exclusive range data can either be provided directly by system 12 or be prepared from the data received by system 12.

System 12 or system 20 optionally and preferably builds a skeleton range image of patient 16 and individual 18 from the range data. Since there is no light intensity information in the range data, patient 16 and optionally also individual 18 cannot be identified from the depth image or skeleton range image. However, it was found by the present Inventors that such an image can be processed to classify skeleton movements and/or postures, for the purpose of monitoring the hygienic activity of an individual in the scene. In particular, the present inventors found that classification of hand gestures allows identifying touch events and also hand hygiene operations performed by the individual.

Preferably, one or more objects or individuals within environment 14 are tagged by markers 26 that are detectable by system 12, and also identifiable by system 20. The tagged objects can include clothing, glove boxes, medical devices, textiles, towels, bed lining, hand cleansing devices, support structures, wall-mounted sockets, computers, monitors, doors, door handles, furniture items etc.

The markers can be of any machine-readable type known in the art, such as, but not limited to, a barcode (e.g. a QR tag), an RFID and an RTLS. When the marker 26 is a barcode, it is adapted to be identified by the wavelength detectable by system 12. For example, when system 12 employs active infrared illumination technique, the barcode is adapted to be readable under infrared illumination.

The markers can optionally and preferably be objects having a unique three-dimensional shape (e.g., star, diamond, chevron, toothed stripe, etc). The spatial resolution of the marker's shape is compatible with the identifiable resolution of system 12 so that the structural features of the marker are acquired while system 12 scans scene 14. The structural characteristics of the three-dimensional shape, optionally and preferably including its size, can be stored in a computer readable library accessible by system 20. Once an image of scene 14 is obtained, system 20 identifies the marker by extracting its structural characteristics from the image and comparing to the entries in the library.

The marker can alternatively or additionally be coated with a material having a sufficiently high (e.g., higher than that of the object or individual being tagged by the marker) infrared reflectivity. These embodiments are particularly useful when system 12 employs active infrared illumination technique for generating the range data. Infrared reflective materials suitable for the present embodiments are disclosed in U.S. Pat. Nos. 3,711,176, 5,103,337, 6,174,360, in U.S. Published Application No. 20030215627, and in Ashwini K. Bendiganavale and Vinod C. Malshe, "Infrared Reflective Inorganic Pigments", Recent Patents on Chemical Engineering, 2008, 1, 67-79, and is commercially available from 3M™, USA.

The marker can be mounted (e.g., attached) on the external surface of the respective object. When the object is other than the skin of the individual, the marker can be embedded in the external surface of the object or be an integral part of the surface of the object. The marker can also be mounted nearby the object, for example, on a wall nearby a socket, or on a pillow nearby the head of the patient. The respective object can also serve as marker by itself, provided its three-dimensional shape is stored in the library. The marker can also be attached to the body or clothing of patient 16 so as to allow system 20 to identify certain parts of the patient's body. Typically, but not necessarily, the marker is attached to the skin or clothing at the vicinity of a region having a high likelihood to contain infection, or a high likelihood to cause infectious disease once becoming infected. Such regions are typically near wound dressings, open wounds, near the entry points of minimally invasive medical devices into the body, and near natural openings of the body.

In some embodiments of the invention data processing system 20 monitors the hygienic activity of individual 18 in scene 14, and in some embodiments of the invention data processing system 20 identifies physical contact between individual 18 and patient 16 and/or between individual 18 and objects in scene 14 and/or between patient 16 and/or objects in scene 14.

Hand hygiene activities identifiable by system 20 include, but are not limited to, hand cleansing, gloves wearing and gloves removals. Hand cleansing can be detected, for example, by identifying rubbing motion of individual. The identification of rubbing motion can be preceded or replaced by identification of a contact between the individual and a hand cleansing device.

Glove wearing can be detected, for example, by identifying finger stretching of a first hand while the fingers of the second hand are not stretched and are in proximity to the wrist of the first hand. The identification of glove wearing can be preceded or replaced by identification of a contact between the individual and a glove box. Glove removal can be identified by identifying motion of the palm of one hand over the palm of the other hand, from the wrist to the fingers. The identification of glove removal can be followed or replaced by identification of a throwing gesture near a waste container. The identification of glove wearing and/or removal can be context-based identification. For example, identification of a medical procedure performed by individual 18 that is likely to precede or follow glove wearing and/or glove removal, can be weighed by system 20 in the determination that a particular gesture corresponds to glove wearing and/or glove removal. For example, when system 20 identifies an operation of fluid extraction performed by individual 18, and then identifies a gesture that may correspond to glove removal, system 20 can determined that it is likely that a glove removal event has been identified. When system 20 identifies a gesture that may correspond to glove wearing, and then identifies an operation of fluid extraction performed by individual 18, system 20 can determined that it is likely that a glove wearing event has been identified.

In some embodiments of the present invention gloves wearing and/or removal is detected by extracting and tracking the color or colors of objects moving with individual 18, accessing a database containing the expected color or colors of the gloves (and optionally also the hands of individual 18), comparing the tracked color(s) with the database color(s), and determining whether or not individual 18 is wearing gloves based on the comparison. These embodiments are particularly useful when the camera comprises a diffuser element placed in front of the color sensors, as further detailed hereinabove. Thus, the color information is preferably collected through the diffuser element so that when the colors are extracted the privacy of the patient and/or individual is maintained. The diffuser element blurred the acquired color image but allows extracting the color of a specific region within the image, such as, but not limited to, the hands.

The present embodiments also contemplate identifying other hygiene activities, such as, but not limited to, wearing and removal of Personal Protective Equipment (PPE), including, without limitation, masks, gowns and full body suits. This can be done similarly to the detection of gloves wearing and/or removal, mutatis mutandis.

A library of gestures corresponding to a plurality of hygiene activities, e.g., hand hygiene activities, can be stored in the memory of system 20 and the identification can be done by comparing the skeleton range image of individual 18 to the gestures of the library.

Physical contact between individuals and/or between an individual and an object can be identified directly and/or by motion analysis. For example, system 20 can analyze the motion characteristics of an individual in the direction of an object or another individual and also analyze the proximity between the two individuals or between the individual and the object.

In some embodiments of the present invention data processing system 20 identifies operation of hand cleansing device 22 by individual 18. This can be done by identifying proximity events between individual 18 and device 22. System 20 can also identify contact events between individual 18 and device 22. When a proximity or contact event is sufficiently prolonged, namely when individual 18 remains in close proximity to device 22 for a time-period that is above a predetermined time-period threshold, system 20 can identify that individual 18 operates device 22. The time-period threshold can be set according to a hand cleansing protocol that is in effect at the facility employing system 10.

The location of device 22 can be determined in more than one way. In some embodiments, system 20 is provided with information regarding the location of device 22 within the environment 14 e.g., during calibration. In these embodiments, system 20 employs image processing to monitor the motion of individual 18 relative to the input location of device 22. In some embodiments, system 20 identifies the location of device 22 by image processing. For example, a marker 26 can be attached to or embedded in device 22 to allow its identification. In these embodiments system 20 employs image processing to determine the locations of individual 18 as well as device 22 so at to monitor the motion of individual 18 relative to device 22.

Device 22 can also be configured to transmit signals pertaining to its operation. For example, device 22 can transmit a signal upon dispensing of cleansing fluid, e.g., a disinfection gel or the like. In these embodiments, system 10 optionally and preferably receives the signals from device 22, for example, via a communication system 24, and determine that individual 18 operates device 22 based on these signals. These embodiments can be combined with the above image processing technique so as to reduce false positive identification. Communication system 24 can employ any type of communication, including, without limitation, WiFi, NFC, Bluetooth, RF, infra red and the like.

Optionally, system 20 identifies individual 18 while individual 18 operates device 22. Since the range image is typically a skeleton range image that does not include light intensity values, the identification is optionally and preferably by means of tagging. In these embodiments, marker 26 is attached to individual 18. During the operation of device 22 individual 18 is identified by system 20 so that the hand cleansing operation can be associated with a particular individual. In some embodiments of the present invention device 22 identifies the marker 26 on individual 18. In these embodiments, marker 26 is adapted to be identified by the wavelength detectable by device 22. For example, when device 22 can detect RF waves, marker 26 can be an RFID. Optionally, device 22 transmits the identification of individual to system 20.

In some embodiments, a sensor 28 is mounted on individual 18. Sensor 28 can be, for example, an alcohol tester that senses the presence of alcohol and transmits a signal responsively to the sensing. Alcohol testers are known in the art and are commercially available, for example, from Dart Sensors Ltd, England. Sensor 28 preferably has a unique ID that is associated with individual 18. The signal transmitted by sensor 28 can include binary information (e.g., 1 for positive sensing and 0 for no-sensing). System 20 communicates with sensor 28, e.g., via communication system 24, and determines whether individual 18 operates device 22 based on the binary information received from sensor 28.

In some embodiments, sensor 28 comprises a movement detector such as a gyroscope and/or accelerometer. In case there is a change in the alcohol level the alcohol sensor sense as well as and there is a movement signature that can be related to a rubbing hands procedure detected by the movement sensors, it can be concluded that individual 18 indeed performs a alcohol hand hygiene procedure. In order to improve reduce energy consumption, the movement detector can be operational at all times while being attached to individual 18, but the alcohol sensing capability is preferably switched off. In these embodiments sensor 28 optionally and preferably comprises a controller. When the movement detector detects a movement that resembles a hand rub movement, the controller switches on the alcohol sensing capability. The alcohol sensor then senses the surroundings and by comparing the current alcohol level in the air to a baseline alcohol level, it can determine whether a hand hygiene procedure is performed. The baseline can be obtained by switching the alcohol sensor periodically in situations that the motion detector does not identify hand rub movement signature. Since sensor 28 is attached to a specific individual, hand rubbing motion that is specific to that individual can be recorded on a memory medium of sensor 28 during calibration.

The data from sensor 28 can be transmitted to system 20 or directly to a central server 56 or it can be transmitted and stored and processed on the Smartphone of the individual. In some embodiments of the present invention sensor 28 is plugged directly to the Smartphone. In this case some of the computational procedures, analytics and storage can be performed on the mobile device and only a portion of the data can be transmitted to the central server by the mobile device.

In some embodiments, sensor 28 also provides location information, so that once the sensor decides that there has been an alcohol hand hygiene procedure, it can signal to system 20 also the location of individual 18 at which the procedure was performed.

In embodiments in which sensor 28 is employed, it is not mercenary for system 10 to include range detection system 12, since information pertaining to the activity of individual 18 can be provided by sensor 28. Nevertheless, in various exemplary embodiments of the invention system 10 comprises range detection system 12 and is also communicating with sensor 28. In this respect, combination of range detection system 12 and sensor 28 can be used to aid the tracking of a certain individual within a plurality of individuals in the same scene. This can be done by correlating the signals received from the motion detectors of sensor 28 with the motion characteristics extracted by system 20 from the range data.

System 10 can therefore relate between an identified individual 18 and location and time at which the identified individual 18 operates device 22. System 10 can optionally and preferably also evaluate the quality of the operation by comparing the duration of the operation with hand cleansing protocol that is in effect at the facility employing system 10.

System 20 can be fed with information regarding how many times, and/or at which times, individual 18 should operate device 22 during the presence of individual 18 in the environment 14. System 20 can log the events at which operations of device 22 are identified and compare the number of events to that information. Based on the comparison system 20 can estimate if individual 18 fulfils the protocol requirements.

In some embodiments of the present invention system 20 identifies access of individual 18 to patient 16, and determines a time window encompassing both the hygienic activity and the access. These embodiments can be employed for determining whether individual 18 has cleaned his hands before accessing patient 16, and also after leaving the patient's bed. Identification of access of individual 18 to patient 16 can be achieved by processing the image and identifying motion of individual 18 in the direction of patient 16 and/or proximity event between individual 18 and patient 16.

As a representative example, when individual 18 belongs to a medical personnel at a hospital room, system 10 can be fed with information that individual 18 should operate device 22 before approaching patient 16, or while moving from one patient to the other. Based on the locations of individual 18 and patient 16 system 10 determines the distance between individual 18 and patient 16 and the duration individual 18 spends near patient 16. System 20 can also determine whether or not individual 18 operates device 22 immediately after entering the environment, and alert when individual 18 fails to do so.

In some embodiments a marker such as marker 26 is attached to the bed 32 of patient 16. In these embodiments, system 20 can identify marker 26 and can determine when individual 18 moves from one identified bed to the other. System 20 can then determine whether individual 18 operates device 22 before approaching the other patient and alert when individual 18 fails to do so.

In some embodiments of the present invention system 20 classifies the interaction of individual 18 with patient 16, and determines a time window encompassing both the hygienic activity and the interaction. The present embodiments contemplate several classes of interaction. A first class of interaction is a contact between the hand of individual 18 and the skin of patient 16. The first class of interaction can be further classified according to the location on the skin at which a contact was identified. Thus, one subclass is a contact with a predetermined organ (e.g., face, lumbus), another is a contact with a wound or other type of opening in the skin. A second class of interaction is a contact between the hand of individual 18 and a medical device 34 nearby patient 16. A third class of interaction is a contact between the hand of individual 18 and a medical device 36 that is in contact with the skin of patient 16. As a representative example, system 20 can identify when a medical personnel member replaces the patient's urine bag by identifying a proximity event or contact between the hand of the medical personnel member and the urine bag.

The above classes of interaction can be identified by image processing, preferably with the aid of one or markers such as marker 26. Specifically, a marker can be attached to the skin of patient 16, to allow system 20 to employ image processing so as to determine a proximity event or contact between the hand of individual 18 and the skin near the marker. Similarly, a marker can be mounted on or be an integral part of device 34 and/or 36 to allow system 20 to employ image processing so as to determine a proximity event or contact between the hand of individual 18 and device 34 and/or 36.

Depending on the identified medical device, the above classification can be used to determine whether individual 18 performs an aseptic task, such as, but not limited to, oral care, dental care, aspiration of secretion, skin lesion care, wound dressing, subcutaneous injection, catheter insertion, opening a vascular access system, preparation of food, preparation of medication, and preparation of dressing sets. In various exemplary embodiments of the invention system 20 determines a time window encompassing both the hygienic activity and the aseptic task, for example, for the purpose of determining whether individual 18 has operated device 22 before performing the aseptic task. Verification of identification of aseptic task can be archived by monitoring the activity of individual 18 before or after an event that is candidate to be aseptic task is identified. For example, when system 20 identifies a glove wearing before such a candidate event and/or glove removal after such a candidate event, system 20 can determine that it is likely that the candidate event is an aseptic task performed by individual 18.

Depending on the identified medical device, the above classification can be used to determine whether individual 18 is exposed to body fluids of the patient. Such exposure can occur, for example, during oral care, dental care, secretion aspiration, skin lesion care, wound dressing, subcutaneous injection, drawing and manipulating of a fluid sample, opening draining system, endotracheal tube insertion, endotracheal tube removal, clearing up urines, clearing up faeces, clearing up vomit, handling waste (e.g., bandages, napkin, incontinence pads), cleaning of contaminated material, and cleaning of areas, such as, but not limited to, lavatories and medical instruments. In various exemplary embodiments of the invention system 20 determines a time window encompassing both the hygienic activity and the exposure to body fluid, for example, for the purpose of determining whether individual 18 has operated device 22 after exposure to body fluids.

In various exemplary embodiments of the invention system 10 is configured to monitor whether the requirements set forth by the hand hygiene protocol published by the World Health Organization known as "five moments for hand hygiene" (see, e.g., Sax H, et al., J Hosp Infect 2007, 67(1): 9-21). According to this protocol hand cleansing is executed at least at the following moments: (i) before patient contact, (ii) before an aseptic task, (iii) after body fluid exposure risk, (iv) after patient contact, and (v) after contact with patient surroundings. Therefore, system 10 optionally and preferably issues an alert when a contact between individual 18 and patient 16 has been identified before or sufficiently long time after (e.g., above 5 minutes after) individual 18 has operated device 22, and/or when individual 18 has not operated device 22 within a sufficiently short time-interval (e.g., less than 5 minutes) after such contact. System 10 optionally and preferably issues an alert when system 20 identifies that individual 18 is performing or is about to perform an aseptic task before or sufficiently long time after (e.g., above 5 minutes after) individual 18 has operated device 22. System 10 optionally and preferably issues an alert when system 20 identifies that individual 18 was exposed to body fluid of patient 16 but has not operated device 22 immediately thereafter. System 10 optionally and preferably issues an alert when system 20 identifies a contact between individual 18 and the objects near patient 16, but does not identify that individual 18 operates device 22 within a sufficiently short time-interval (e.g., less than 5 minutes) after such contact.

In any of the above embodiments, when system 20 determines that the requirements of the hand cleansing protocol that is in effect at the facility employing system 10 are not fulfilled, system 10 can issue an alert signal, using an alert device 30. The alert can be addressed to individual 18, for example, by sending an alert signal to a mobile device (e.g., Smartphone, a designated beeper, a designated visual indicator display, etc.) carried by individual 18, and/or to a central monitoring location that supervises fulfillments of procedures and protocols. Other alerting techniques are described hereinunder. System 20 can also log statistics pertaining to hygienic activity, store the statistics on a non-transitory computer readable medium, and/or to transmit the statistics to a central computation server. For example, system 20 can log events at which hand cleansing is identified, and also log failures to perform hand cleansing for further analysis.

The events collected by system 20 can be used for analyzing the regiment of hand hygiene for all or some of the individuals in the medical facility. Thus, a plurality of systems such as system 10 can be deployed in the facility (e.g., at separate hospital rooms). Each system can transmit data pertaining to hand cleansing events of the individuals, and also data pertaining to classified contact events between the individuals and the patients and/or individuals and medical devices, as further detailed hereinabove. At a central computation server 56, the events can be analyzed to determine, for each individual, whether two contact events are separated by at least one hand cleansing event. Server 56 can be a local server or it can be a cloud computing resource of a cloud computing facility, in which case server 56 communicates with system 10 via a communication network.

A report regarding the analysis can be then be issued and displayed on a display device or stored on a computer readable medium. In some embodiments of the present invention the server also calculates a score based on the analysis. For example, the score can reflect the number of identified failures to perform hand cleansing (a penalty score), or the number of identified hand cleansing events (a credit score) or a combination of a penalty score and a credit score as known in the art. For example, denoting the penalty score by P and the credit score by C, where P and C are non-negative and at most 1, a total credit score can be proportional to $P+(1-C)$. The score can be used, for example, for ranking a plurality of medical facilities.

In some embodiments of the present invention the hand hygiene performances and achievements are collected from different healthcare units and facilities, substantially in real time. The server can store and analyze the collected data, for example, from the standpoint of the five moments for hand hygiene (5MOHH) protocol. The server can track changes in the amount of Healthcare-associated Infections (HAI) of each facility and the like. Once all this data is analyzed, this information (the entire information, or only part of it, based on the definitions each healthcare facility will choose) can be sent back to the facilities for presentation on interactive screens placed in different locations in the facilities. The information can also be presented to the individuals and patient visitors in the facilities. The information can be in the form of graphs, graphical images, text, animations and the like.

A facility employing system 10 can present information pertaining to the analysis on displays in its unit wards. Each display can present the 5MOHH performances, 5MOHH hand hygiene counters, and hand hygiene statistics of a specific unit, optionally and preferably in real time, compared with the relevant performances and achievements of other facilities that use system 10. In such a way the employees and visitors can see how they contribute to the performances of the local facility as compared to other facilities. Creating a constructive positive competition among the healthcare facilities allows to increase compliance with the 5MOHH hand hygiene procedures, to keep the workers awareness to the hand hygiene always high, and eventually to reduce HAI and infections rate low. Healthcare providers and workers can be rewarded for their proper hand hygiene improvement and achievements with accordance to the 5MOHH standard. Such interactive platform can keep the employees and visitors awareness to the 5MOHH standard for a long period of time, and can improve healthcare employee compliances with the 5MOHH standard. The different data types presented on the displays can be also be presented or sent to employee's mobile phones or to their personal computers.

The events collected by system 20 can also be used for determining the productivity of individual 18. For example, the number of contacts between individual 18 and patients and/or the number of contacts between individual 18 and medical devices over a time period (e.g., several hours) can be determined. The numbers can be compared to a predetermined threshold or to the average numbers obtained for other individuals in the same or other facilities. Based on the comparison, the productivity of individual 18 can be determined. Optionally, a productivity score that relates to the number of contacts is calculated and assigned to individual 18 to quantify the productivity. The procedure can be executed for a plurality of individuals that are employed in the same or different facility, and the individuals can be ranked according to their productivity scores.

Figure 2A:
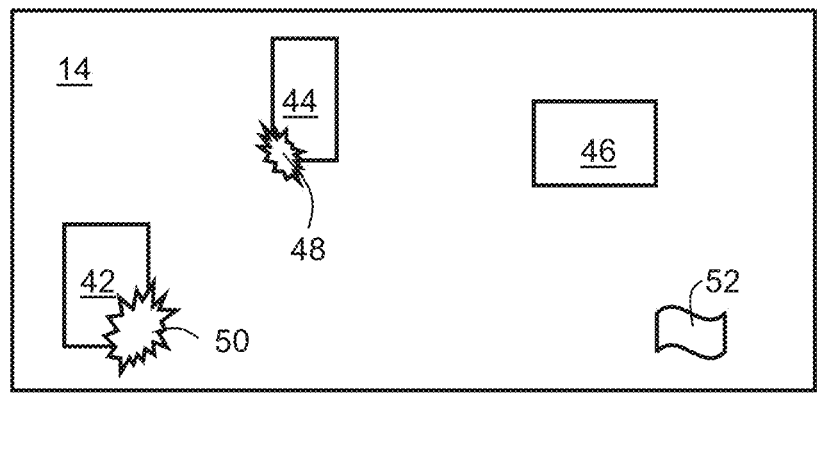
FIGS. 2A-C are schematic illustration of a mapping process, according to some embodiments of the present invention.
Figure 2B:
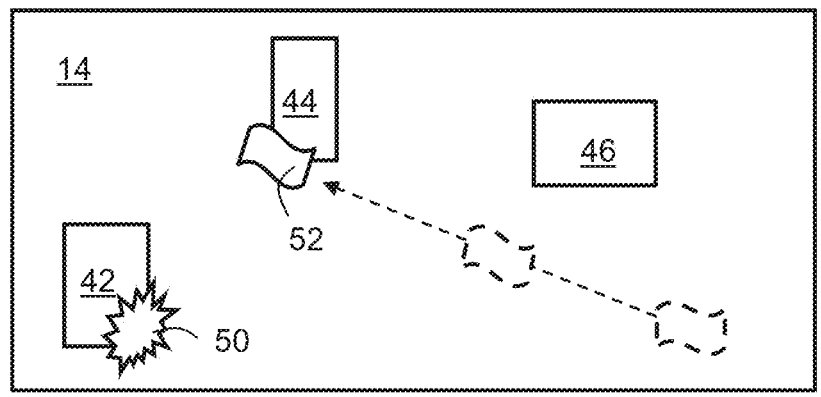
Figure 2C:
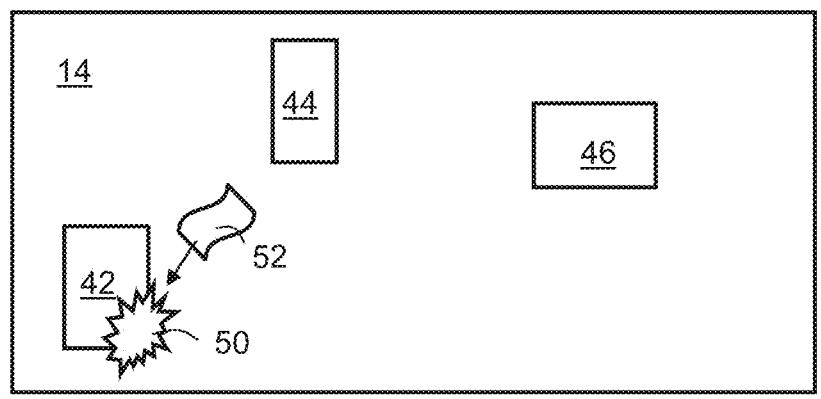

In some embodiments of the present invention system 20 identifies points of contact between an individual (e.g., individual 18 patient 16) and objects in scene 14, and maps these points of contact, preferably their 3D coordinates (e.g., Cartesian coordinates) over scene 14. A representative example of such a mapping is illustrated in FIGS. 2A-C. Shown in FIGS. 2A-C is a map 40 of scene 14 including some objects 42, 44 and 46, any one of which can be any of the objects described above. Objects 42, 44 and 46 are detectable by system 12, hence can be mapped by system 20 in relation to the borders of scene 14. Objects 42, 44 and 46 can be detectable either by virtue of their surface reflectivity and/or by means of markers such as marker 26 (not shown, see FIG. 1) that may be attached to the external surface of the respective objects. Once system 20 identifies a contact between the individual and one of objects 42, 44 and 46, system 20 preferably marks the point of contact on map 40. Such markings are shown in FIG. 2A at 48 and 50.

Objects 42, 44 and 46 can also be detectable by virtue of their height. The range image provided by system 12 can be analyzed to identify the floor level, and a contact between the individual and any object that has a height above the floor level which is above a predetermined height threshold can be marked. The predetermined height threshold can be zero in which case any contact between the individual and an object that is not at the floor level is marked.

Objects 42, 44 and 46 can also be medical devices on patient body or body organs. In this case Map 40 can also represent contaminated surfaces and points on patient body and not only on the environment.

Map 40 therefore represents the condition of the environment from the standpoint of infectious areas. Since hands collect bacteria at almost every touch and can move the bacteria from one place to another, increasing the number of hand contacts in a specific location increases the probability that this area may contain infection and bacteria. Thus, the shape, color and/or size of the markings on map 40 is optionally and preferably selected based on a statistics regarding the number of identified contacts with or near the respective point-of contacts. For example, a location at which a higher number of contact events can be marked with darker color, and a location with fewer number of contact events can be marked with a brighter color. The shape, color and/or size of the markings on map 40 can also optionally and preferably vary with time, according to an expected bacteria growth rate.

Map 40 can be used in more than one way.

In some embodiments, system 20 transmits map 40 to a central location thereby providing a report regarding the condition of the respective environment. In some embodiments, system 20 tracks a cleansing device 52 in the scene and updates map 40 responsively to the tracking. Cleansing device 52 can be a hand held cleansing tool, or controlled propelled device or an autonomous device, such as a robot or a robotic arm. Cleansing device 52 preferably comprises an antiseptic or antibacterial material, that can be in the form of a fabric loaded with an antiseptic or antibacterial agent, an aerosol device having container filled with the antiseptic or antibacterial agent, and the like. When system 20 identifies contact between cleansing device 52 and one of the marked points of contacts (FIG. 2B), system 20 removes the respective marking (marking 48 in the present example) from map 40 (FIG. 2C).

When map 40 is provided to an autonomous system, the autonomous system can react to the contact history. System 20 can detect period of times where there are no visitors or other individuals in the environment. In order to allow the robot or autonomous system perform its duties without interacting with the individuals, the autonomous system or robot can be programmed in such a way that it starts to perform its duties only after all the individuals leave the environment. Alternatively the autonomous system can decide where to perform its disinfection operations in areas that are sufficiently far from the location of the individuals.

Figure 3:
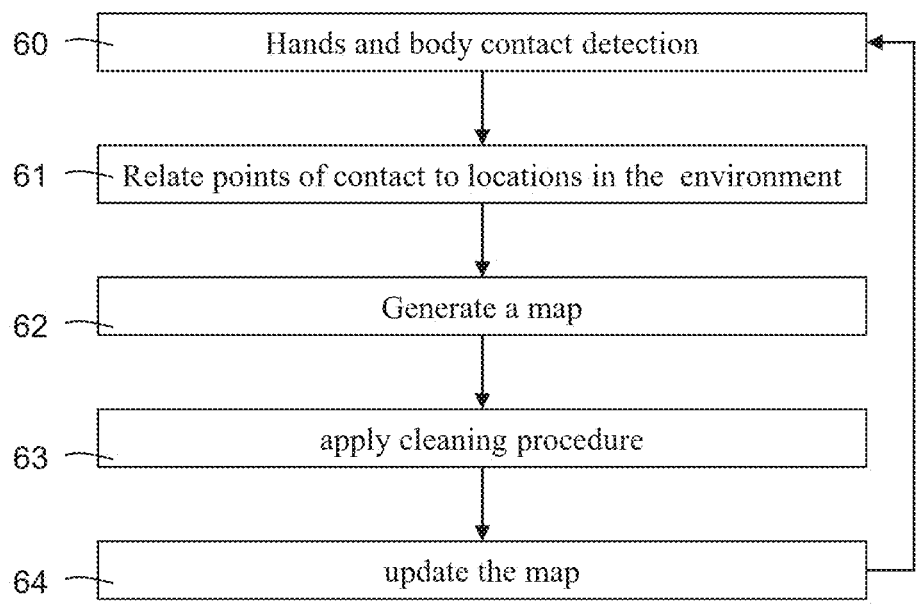
FIG. 3 is a flowchart diagram describing a map updating procedure according to some embodiments of the present invention.

A flowchart diagram describing such a procedure is provided in FIG. 3. At 60, hand and/or body contacts are detected, at 61 the contact points are related to locations in the environment, at 62 a map is generated, at 63 a cleaning procedure is employed and at 64 the map is updated.

In these embodiments, cleansing device 52 is identifiable by system 20. For example, device 52 can be made of a material and shape detectable by system 12, and system 20 can identify device 52 by means of image processing as further detailed hereinabove. Alternatively or additionally a marker such as marker 26 can be mounted on device 52, so that device 52 is identified through the marker attached thereto. In some embodiments, device 52 is equipped with an indoor position sensing system that allows device 52 to transmit its location to system 20. System 20 can receive the location information from device 52, register the information with respect to map 40 and update map 40 accordingly.

In some embodiments of the present invention a motion detector is mounted on or attached to cleansing device 52. The motion detector can transmit signals to system 20 that can process these signals to determine the location of device 52 based on its motion characteristics. Preferably, the data from the motion detector is correlated with the data from system 12. Such correlation can provide a more accurate determination of device 52 in the environment.

When cleansing device 52 is a controlled propelled device, or an autonomous device or a robotic device, system 10 optionally and preferably signals device 52, for example, via a control circuit 54 (see FIG. 1), to access and disinfect the points of contact at 48 and 50.

Map 40 can optionally and preferably be overlaid on top of a 3D model of the environment, or on top of an image acquired by one or more of the cameras views. Map 40 can be used as a directive to healthcare personal to the location where infection may be exist and grow. An individual that cleans the respective environment can receive a signal from system 10 when the individual is near a location that corresponds to a marked spot on map 40.

Figure 4:
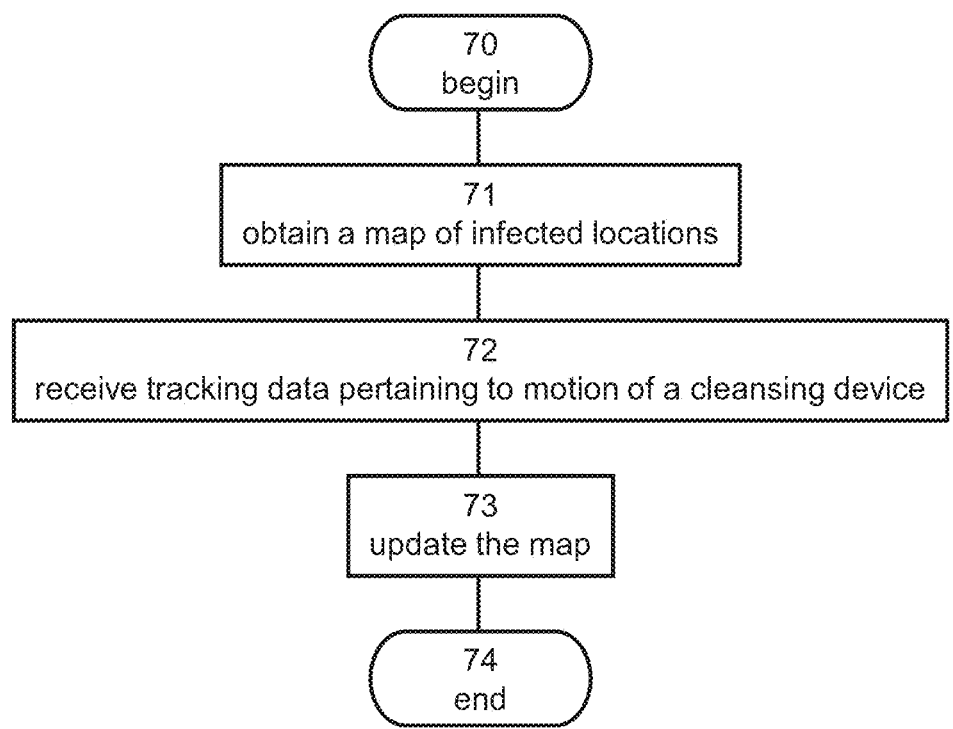
FIG. 4 is a flowchart diagram of a method suitable for monitoring a condition of a medical environment, according to some embodiments of the present invention.

FIG. 4 is a flowchart diagram of a method suitable for monitoring a condition of a medical environment, according to some embodiments of the present invention. The method begins at 70 and continues to 71 at which a map of the environment such as map 40 is obtained. The map comprising locations in the environment identified as being infected. The method continues to 72 at which tracking data pertaining to motion of a cleansing device, such as device 52 in relation to the locations is received. The method continues to 73 at which the map is updated based, at least in part, on the tracking data, as further detailed hereinabove. The method ends at 74.

In some embodiments of the present invention the method generates the map by monitoring points of contact between individuals and objects in the environment. In some embodiments of the present invention the method transmits the updated map to a central computation server. In some embodiments of the present invention the method receives the tracking data by receiving signals generated by the cleansing device. In some embodiments of the present invention the method receives the tracking data by receiving signals reflected by the cleansing device. In some embodiments of the present invention the method receives the tracking data by optically scanning the environment to determine a location of said cleansing device. In some embodiments of the present invention the cleansing device is a robotic cleansing device and the method controls the robotic cleansing device to access and disinfect the points of contact.

Figure 5:
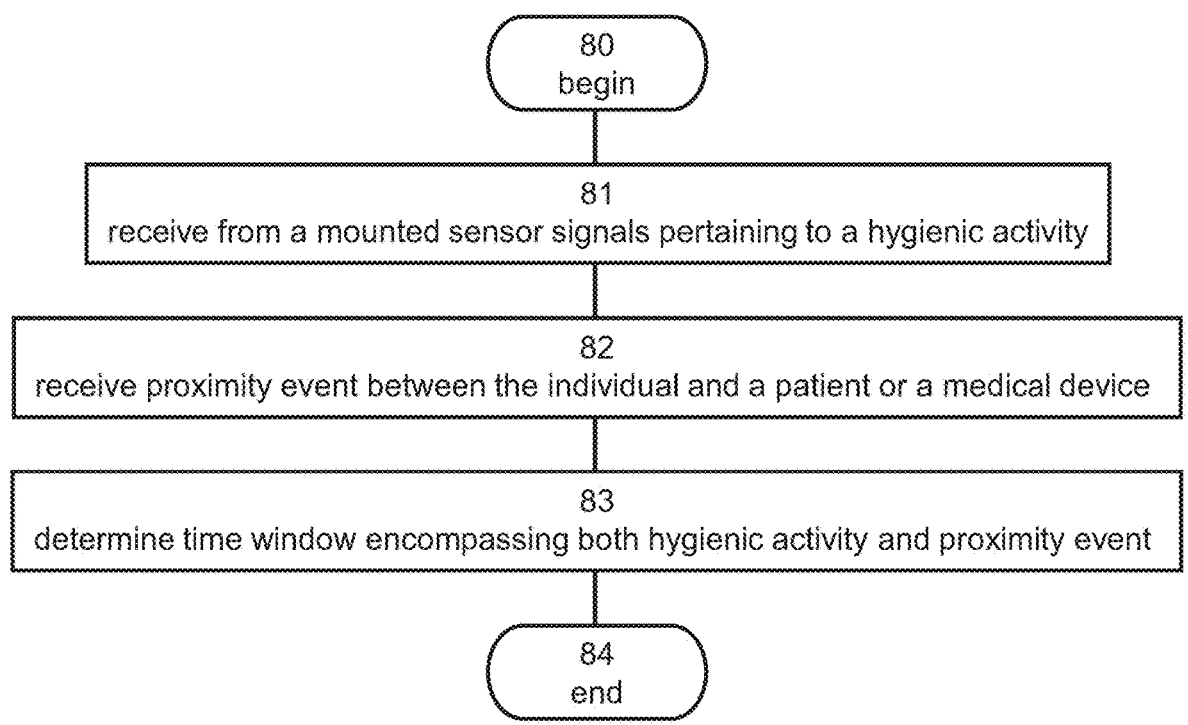
FIG. 5 is a flowchart diagram of a method suitable for monitoring a hygienic condition of an individual, according to some embodiments of the present invention.

FIG. 5 is a flowchart diagram of a method suitable for monitoring a hygienic condition of an individual, according to some embodiments of the present invention. The method begins at 80 and continues to 81 at which signals pertaining to a hygienic activity of the individual or lack thereof are received from a sensor mounted on the individual. The sensor can be of any type including, without limitation, a chemical sensor, an optical sensor and a mechanical sensor. In some embodiments of the present invention the sensor is sensor 28 as further detailed hereinabove.

The method continues to 82 at which proximity data including a proximity event between the individual and a patient or a medical device is received. The method can receive the proximity data by receiving signals generated or reflected by the medical device. The method can receive the proximity data by optically scanning the environment to determine a location of the individual and a location of the patient and/or the medical device, as further detailed hereinabove. The method continues to 83 at which a time window encompassing both the hygienic activity and the proximity event is determined, as further detailed hereinabove. The method ends at 84.

Figure 6:
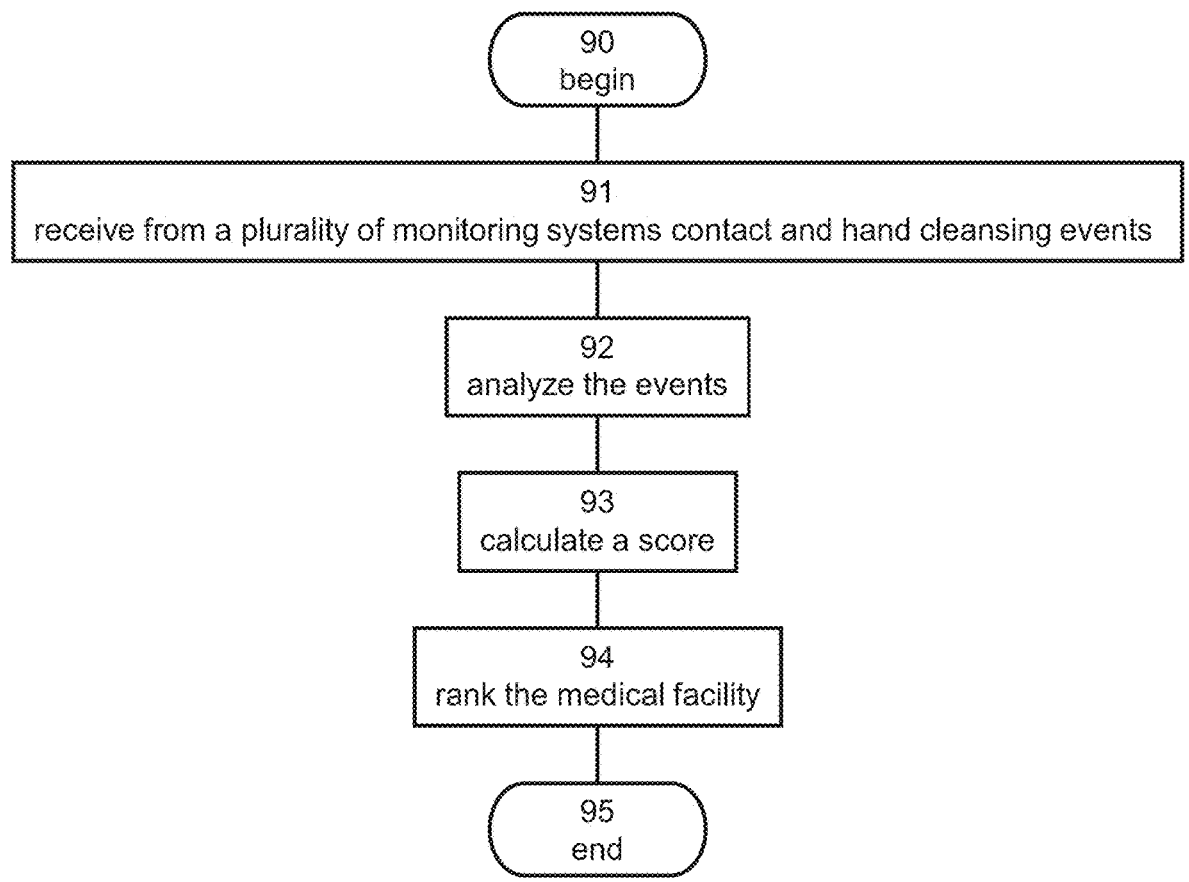
FIG. 6 is a flowchart diagram of a method suitable for monitoring a hygienic condition of an individual, according to some embodiments of the present invention.

FIG. 6 is a flowchart diagram of a method suitable for analyzing a regiment of hand hygiene for a plurality of individuals in a medical facility, according to some embodiments of the present invention. The method begins at 90 and continues to 91 at which data pertaining to hand cleansing events of the individuals, and classified contact events between the individuals and patients and/or medical devices is receive from a plurality of monitoring systems, as further detailed hereinabove. The method continue to 92 at which the events are analyzed, for example, at a central computation server, to determine, for each individual, whether two contact events are separated by at least one hand cleansing event. The method continues can issue a report regarding the analysis is issued. The method optionally and preferably continues to 93 at which a score is calculated based on the analysis. The method is optionally and preferably executed for a plurality of medical facilities. In these embodiments, the method can continue to 94 at which the medical facilities are ranked according to the scores. The method ends at 95.

It was found by the Inventor that while a touch event between the individual and the patient can be identified by analyzing the range data, there are some less than optimal scenarios that are better be avoided. For example, when the environment includes many obstacles, (furniture's, medical equipment etc.) and/or when the individual or patient 16 does not stands in front of the range sensor or when individual 18 or patient 16 stands in front of the depth sensor and slightly stretch forward his hand toward the depth sensor and/or when the range data obtained by system 12 is based on a top view of individual 18 or patient 16, and/or when the hand of individual 18 is already in proximity to the body of patient 16. In such scenarios, the sensor captures only part of the individual body (for example, side view or top view), mistakenly detects other objects that resemble the shape of the individual's limb or palm, or fails to detect the 3D location of a part of the individual's body (e.g., limb, palm, etc.). Another less than optimal scenario is a situation in which multiple healthcare individuals are in the environment.

The above problem can be solved by placing the sensor at the vicinity of the bed. It this case, a plurality of sensors are employed so as to cover the patient zone and monitor the individual approaching the patient from both sides of the patient bed (side 201 and side 200). It was nevertheless found by the inventor that use of a plurality of sensors may generate crosstalk between the range sensors, and may also be a configuration that is complex to deploy, e.g., in dense environments. The inventor also found that the above solution narrow the size of sensing region to the overlap between the field-of-view of the sensors, so that for monitoring larger regions there is a need to deploy more than two sensors.

The present embodiments also contemplated identification of contact between individual 18 and the patient's body by means of marker 26. In these embodiments marker 26 is preferably placed on the hand of individual 18. Typically, but not necessarily, marker 26 is in the form of a bracelet or a glove worn on the wrist, forearm or palm of individual 18. Alternatively, marker 26 can be attached to the sleeve of the individual's clothing. The advantage of these embodiments is that they allow accurate and reliable identification of a touch event by analyzing the distance between the marker on the hand of the individual and the patient's body, more preferably between the marker on the hand of the individual and a specific location on the patient's body, for example, at the location of device 36 in contact with the skin of patient 16. Preferably the touch event is identified by calculating the distance between marker 26 on the hand and device 36 on the body. Another advantage of placing marker 26 on the hand is that it allows identifying touch event even when the touch occurs during motion of patient 16 and/or individual 18.

Identification of touch event using marker 26 can be based on range data received from a single range sensor from a single view point. The single range sensor provides a single view point, such as, but not limited to, a side view 200, 201 or a back view 202 (generally behind the head of the patient) or a front view 203 (generally at the leg side of the patient) or a top view 204 above the bed 32.

Preferably, marker 26 is identifiable. This can be done by providing market 26 with an identifiable 3D structure, or a pattern identifiable by illuminating infrared light, or by providing market 26 with an infrared light source that transmits an identifiable pattern.

Placing marker 26 on the hands of the individual (e.g., on the wrist or on the forearm) allows an accurate and reliable hand touch detection, not only for the bed configuration shown in FIG. 1, but also at any other scenarios, either for hand hygiene methodologies or for environmental hygiene (and disinfection) methodologies which are both require accurate, stable and reliable hand touch detection. Such strategy of placing marker 26 or marker 28, on the hands of the individual or on the wrist or on the arm just below the elbow of the individual 18 or patient 16 also extends the detection range and field of view of the range 3D sensor.

When marker 26 is placed on the forearm the distance between the marker and the palm, wrist or elbow may be estimated once the range sensor detects the hand of individual 18. Once this distance is obtained, the location of the wrist, or more preferably the palm of individual 18 can be approximated by adding this distance to the location of marker 26.

Thus, the present embodiments provide accurate and reliable technique for the identification of touch event using a single range sensor from a single point of view, which technique maintains the privacy of the patient. Touch events between individual 18 and other objects can also be identified similarly.

In some embodiments of the present invention marker 26 can be used to train system 10 to identify the location of the individual's hand once the marker is removed from the hand. In these embodiments, a look-up table is optionally and preferably created, wherein each entry of the lookup table is associated with a location of individual within scene 14 and stores the spatial vector between the location of the hand as estimated by tracking marker 26 and the location of the hand as estimated without tracking marker 26. Such a lookup table can then be used for estimating the location of the hand of individual 18 once marker is removed. Specifically, system 10 can determine the location of individual 18 within scene 14, retrieve the stored spatial vector from the respective entry of the lookup table, estimate the location of the hand of individual 18, and correct the estimate based on the retrieved spatial vector.

In some embodiments of the present invention each entry of the lookup table is subdivided into subentries corresponding to geometrical parameters describing the individual 18 at the respective location in scene 14. Such geometrical parameters can include, but are not limited to, orientation and posture of the body of individual 14. It these embodiments, system 10 determines the location of individual 18 within scene 14 as well as the geometrical parameters, retrieves the stored spatial vector from the respective subentry of the lookup table, estimate the location of the hand of individual 18, and correct the estimate based on the retrieved spatial vector.

Once a touch event is identified system 10 optionally and preferably determines whether a hand hygiene operation has been performed as further detailed hereinabove. When system 10 determines that no hand hygiene operation has been performed (or not performed according to a predetermined timing protocol) system 10 preferably issues an alert signal. The alert signal can be of any sensible type, such as, but not limited to, an audio signal, a visual signal and a textual signal. When system 10 determines that no hand hygiene operation has been performed before the touch event, the alert can include indication to provide an extra care, e.g., a disinfection procedure, to the touched patient. Suitable types of alert signals are described hereinunder.

Figure 7:
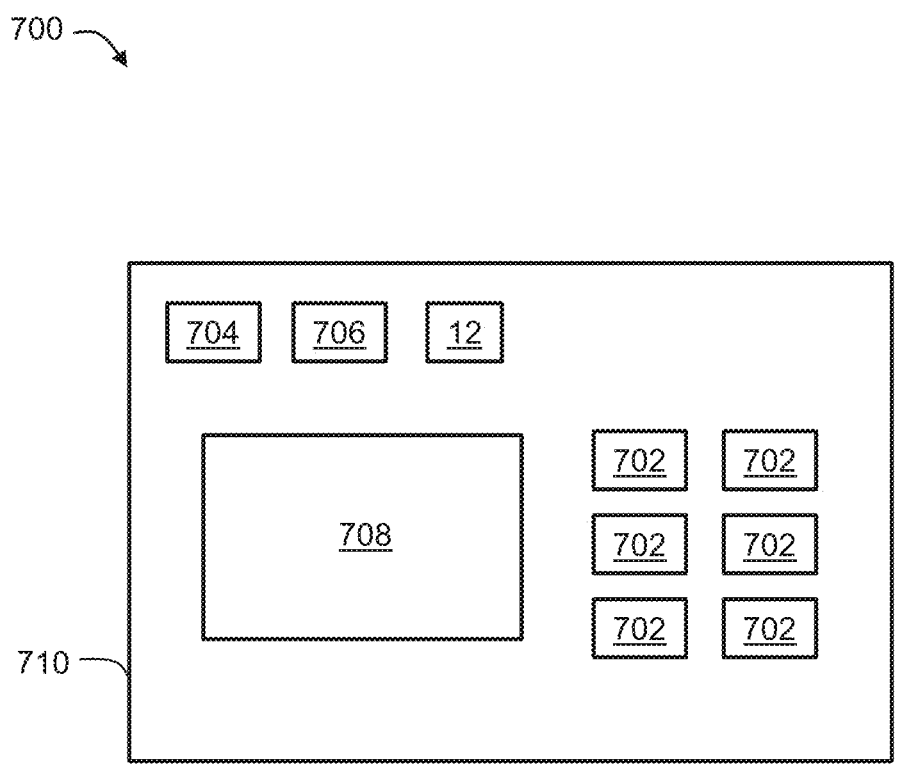
FIG. 7 is a schematic illustration of an interactive vending system 700 according to some embodiments of the present invention.
Figure 8A:
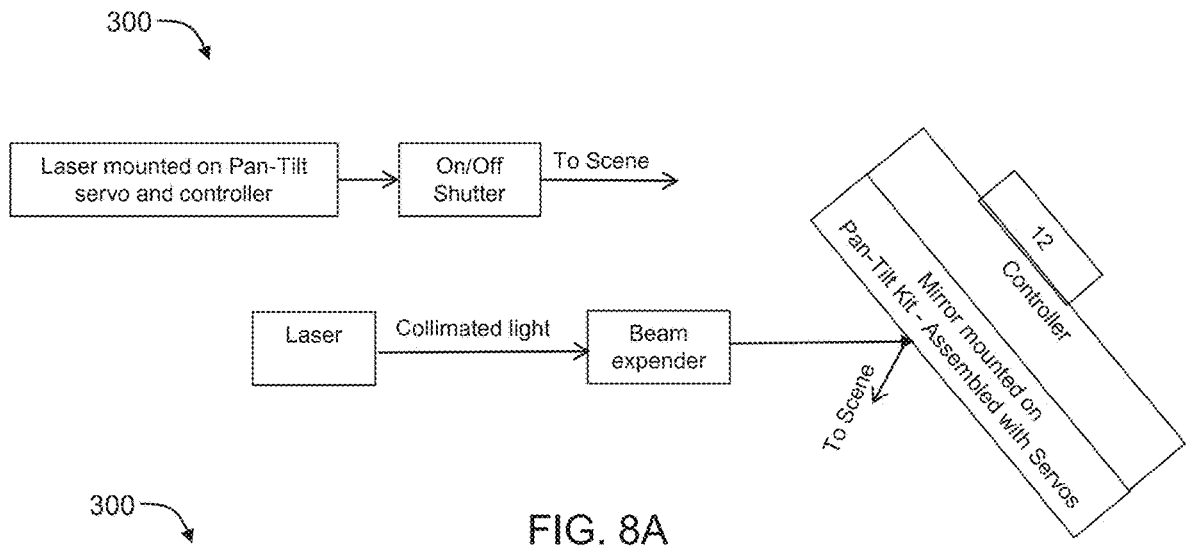
FIGS. 8A-H are schematic illustrations of exemplary setups for an electromagnetic signaling system, according to some embodiments of the present invention.
Figure 8B:
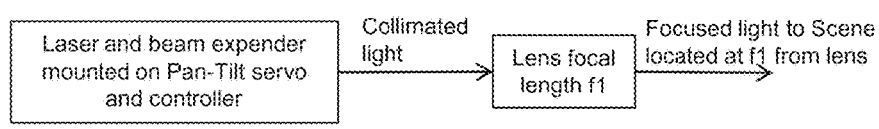
Figure 8C:
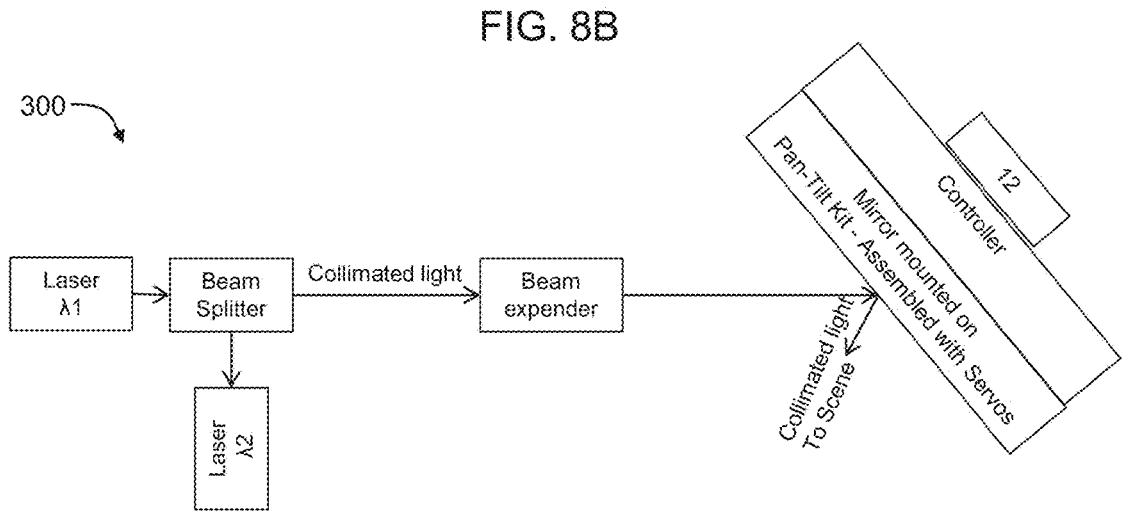
Figure 8D:
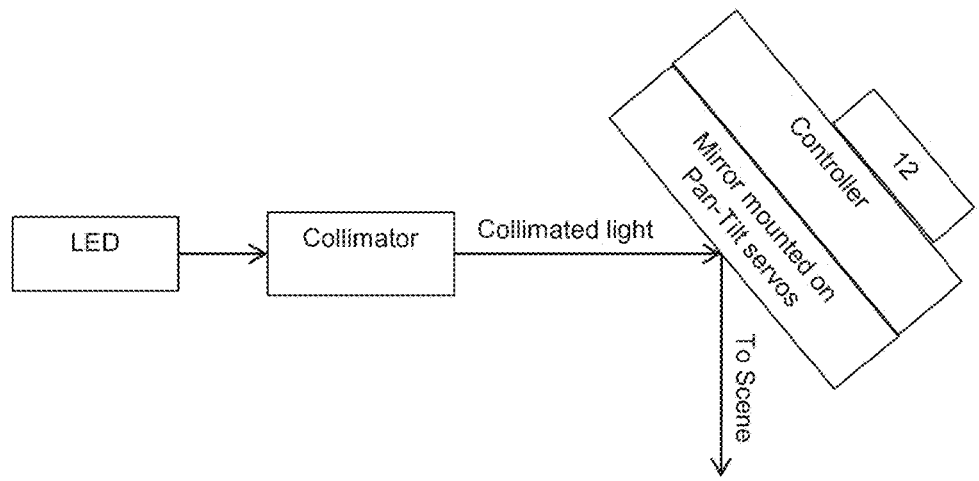
Figure 8E:
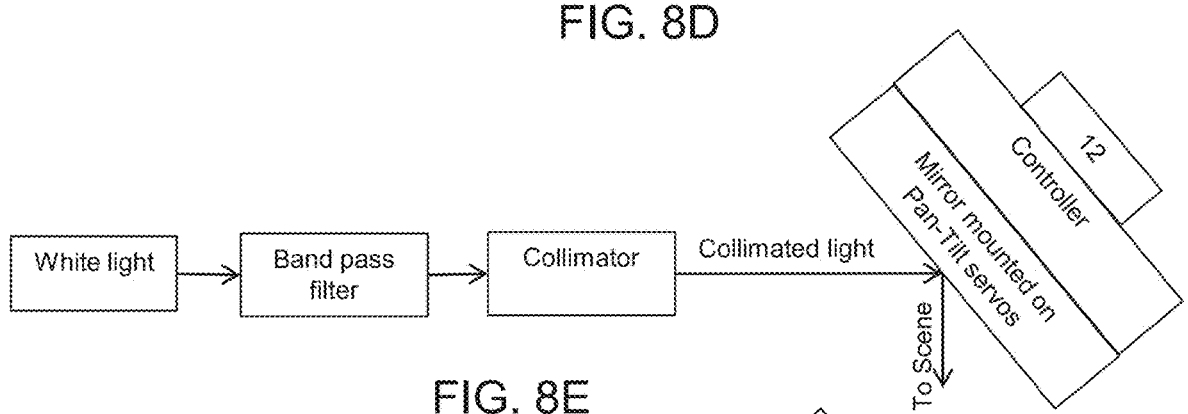
Figure 8F:
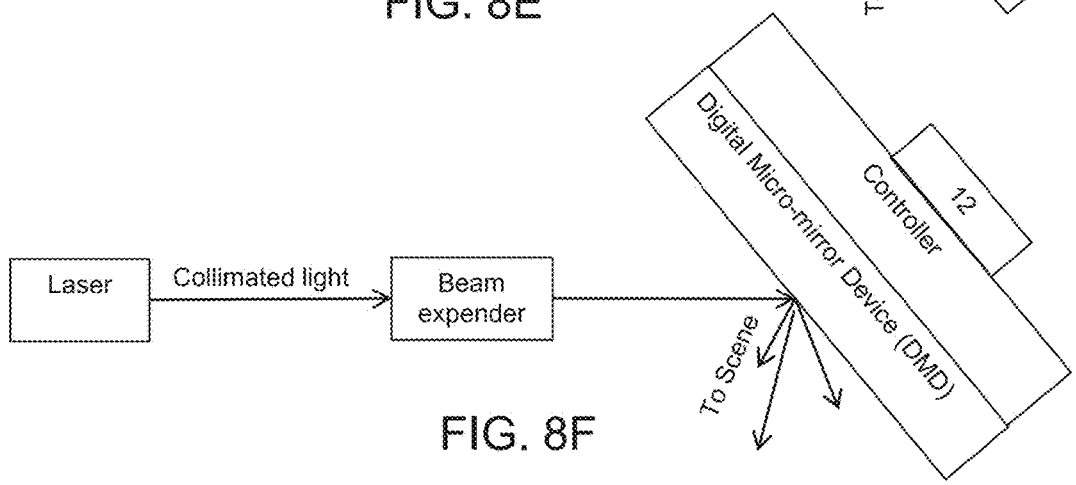
Figure 8G:
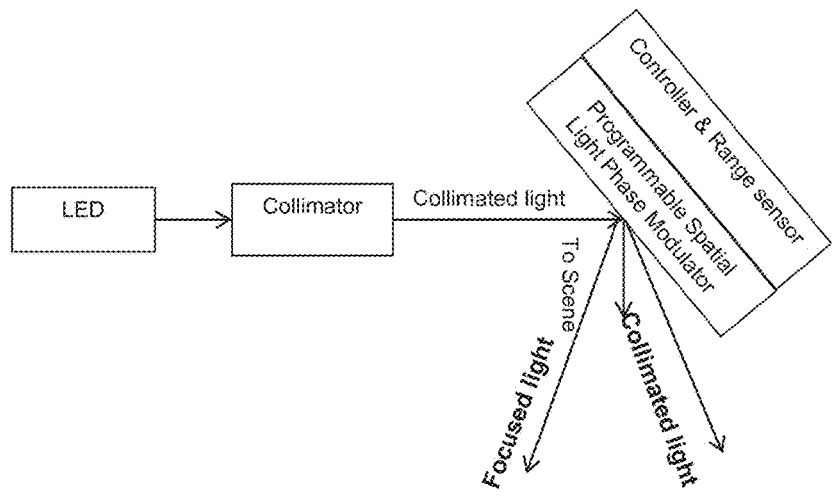
Figure 8H:
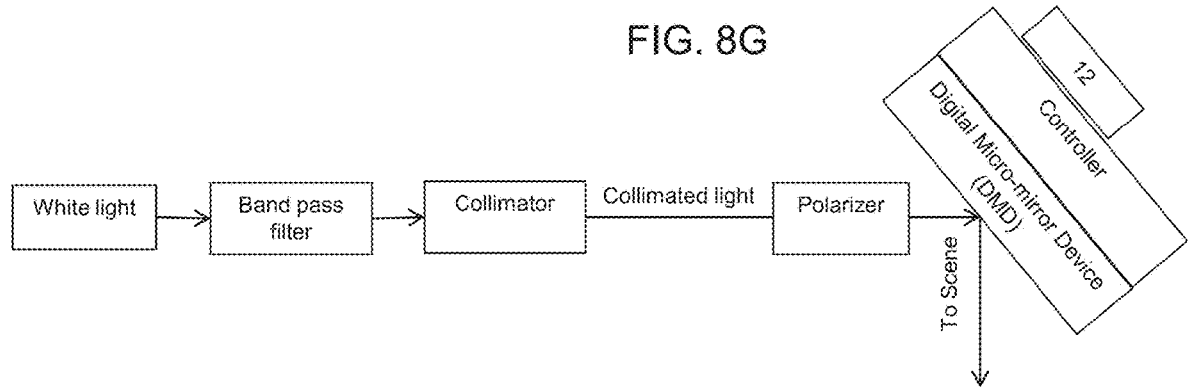

FIG. 7 is a schematic illustration of an interactive vending system 700 according to some embodiments of the present invention. Vending system 700 typically provides hygiene products such as, but not limited to, as antiseptic wipes, antiseptic foam, antiseptic liquid. Vending system 700 can alternatively or additionally provide other products, such as, but not limited to, beverages, food products, and the like. System 700 comprises a user interface 704, a control circuit 706 and one or more vending compartments 702. Once the operator selects a product via user interface 704, a signal containing information regarding the selection is transmitted from user interface 704 to control circuit 706. Control circuit 706 transmits a control signal to one or more of vending compartments 702, through which the user receives the selected products.

System 700 optionally and preferably comprises a range detection system (such as, but not limited to, range detection system 12), or an imaging system (such as, but not limited to, a camera). System 700 preferably also comprises a display device 708, which is also controlled by circuit 706 and which provides the operator with information pertaining to the hygiene state of system 700 and/or the user. System 700 can be positioned in healthcare facilities, doctor clinics or hospitals. System 700 can also be positioned in other public place, such as, but not limited to, airport terminals, public transportation stations, education institutes, banks, restaurants, public restrooms, etc. The range detection or imaging system, and/or the display device can be embedded in the enclosure 710 of system 700 as integral part of the vending machine, as well as may be separated from the vending machine.

Following are several examples for operation mode of system 700.

In one example, the user purchases from system 700 a hand hygiene antiseptic foam and performs the activity of hand hygiene. The activity can be presented on device 708.

In another example, once the user approaches system 700, display 708 presents the user with information describing point of contacts between other individuals and on system 700, preferably user interface 704. Such information can be retrieved, for example, as described above with reference to FIGS. 2A-C. The information is useful to the user since such point of contacts may be infected with, for example, bacteria. Once a cleansing device (e.g., device 52) is used to clean the point of contacts, system 700 can update the information displayed so as not to include the respective points.

In another example, display 708 presents a map such as map 40, describing the condition of the environment in the vicinity of system 700 from the standpoint of infectious areas. The map can be presented at all times, or in response to a receipt of a cleansing device via one of compartments 702.

Following is a description of a technique suitable for alerting, for example, when the requirements of the hand cleansing protocol that is in effect at the facility employing system 10 are not fulfilled. The technique is based on projection of a light beam (e.g., laser light or white light) onto a predefined surface or object. This is advantageous since the projected light captures the attention of individual 18 more efficiently than other alerting techniques.

The light beam is preferably projected by means of an electromagnetic signaling system 300 which projects a light beam, such as a safe low-power class 1 laser pointer, or a collimated light from a Light Emitting Diode (LED) or a minimal divergence LED light, or a collimated white-light point, onto a predefined surface or objects in the scene. Once individual 18 or patient 16 observes the reflection of the light beam off the surface or object, his or hers attention is captured.

Figure 9:
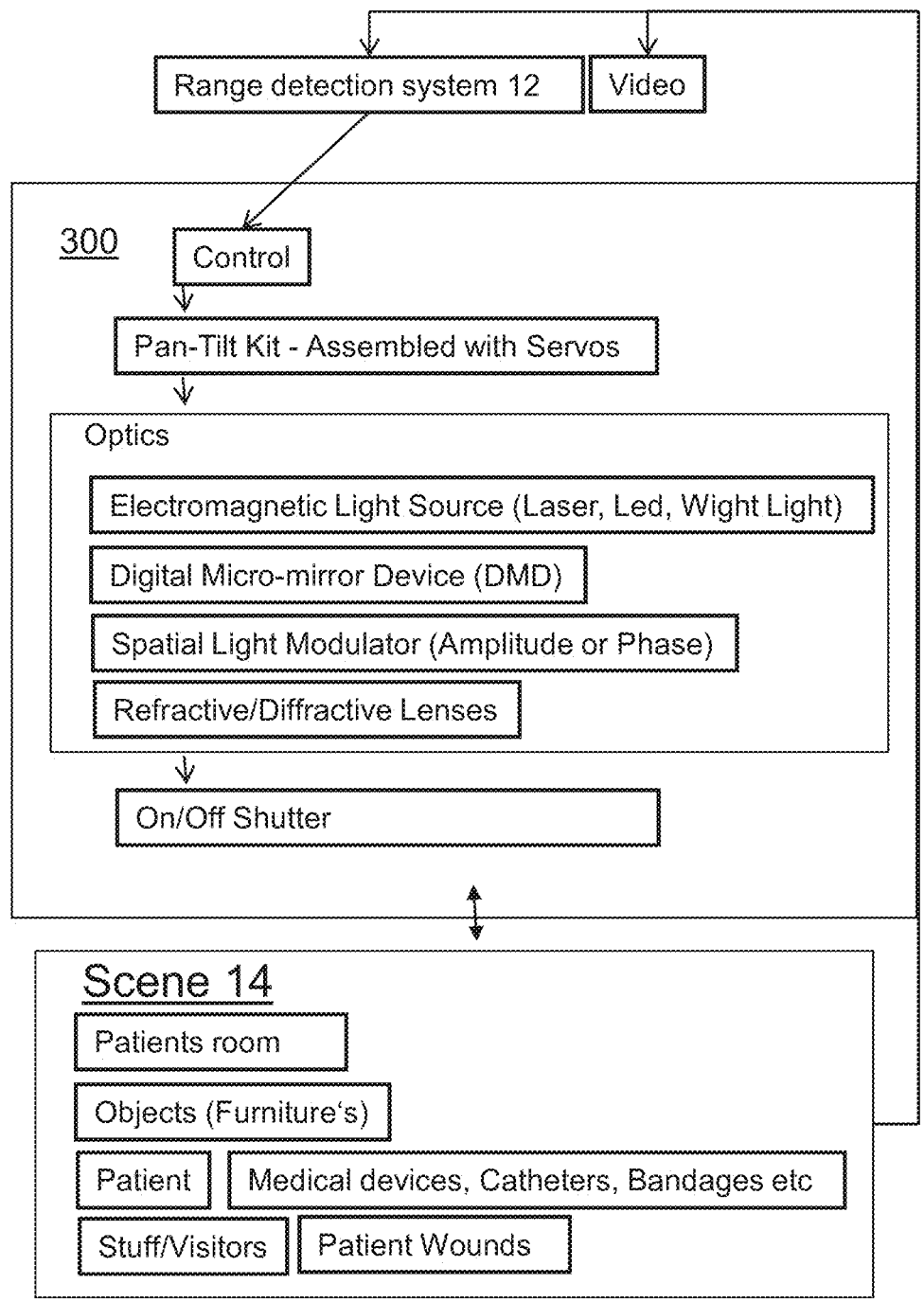
FIG. 9 is a block diagram of an electromagnetic signaling system, according to some embodiments of the present invention.

The alerting technique employed by system 300 can include extracting the 3D location of the different objects (such as medical devices, catheters, individual 18 or patient 16 hands, door knobs, computers etc.) in the environment using system 12, and focuses a light beam 302, onto one or more of those objects. A block diagram of system 300 according to some embodiments of the present invention is illustrated in FIG. 9 and exemplary setups for system 300 which are not to be considered as limiting, are illustrated in FIGS. 8A-H.

System 300 comprises a controller that control servos (e.g., a Pan-Tilt Kit assembled Servos) that control a Light Source. The controller synchronizes between the orientation of the system 300 point of view or its optical axis, and/or the orientation/optical axis of the range sensor and the orientation/optical axis of the Pan-Tilt Kit assembled Servos. The controller then calculates the angle or location of each object captured by system 12 to the relevant pan-tilt angle that is observed by system 300 point of view. The pan-tilt servos control the direction of the light beam either directly or by means of a light redirector, e.g., a mirror, an array of mirrors (e.g., an array of mirrors on a spinning wheel) or a Digital Micro-mirror Device (DMD), a Spatial Light Modulator (SLM), in response to a signal from the controller, so as to project the light beam onto the selected surface.

For example, assume that system 12 has M depth pixels on its horizontal axis and N depth pixels on its vertical axis. The synchronization process between the optical axis of system 12 and system 300 and the servos may be obtained by pointing the laser pointer, placed on the servos, to the specific location of the 3D pixel captured by system 12 at its M/2 and N/2 pixel location. The field-of-view of system 12 includes a matrix of 3D vectors from the 3D scene to the location of system 12. Each type of system 12 has different 3D vector matrix that may be saved in a look-up table. Once system 300 and system 12 share the same optical axis, system 300 can direct the angles of the servos to the relevant angle of the vector represented by the pixel.

In a case in which system 300 and system 12 do not share the same optical axis, and the angle θ between their two optical axes is known, the 3D vector matrix can be adjusted according to θ. The light source preferably projects a light beam in a wavelength that can be detected by system 12, so that a synchronization between the field-of-view of the servos and the field-of-view of system 12 can be obtained. Since a range sensor can detect the heads in the scene, the event that the light beam is pointed towards the eyes of individual can be prevented.

System 300 may optionally and preferably comprise a shutter controlled by the controller that allows the light signaling to reach the scene only when desired. System 300 may optionally include additional optics such as beam expanders, refractive and/or diffractive lenses, an array of mirrors (e.g., an array of mirrors on a spinning wheel), DMD, SLM (Amplitude or/and Phase) as illustrated in FIGS. 8A-H. The additional optics may allow system 300 to project focused light beam that is safe and clear. The additional optics may be configured to provide multiple light beams at the same time, for example, to signal multiple individuals simultaneously. The additional optics may be configured to provide create different light patterns or to create multiple pointing capabilities at different objects and surfaces simultaneously.

The DMD and the SLM may also allow programmable pan-tilt capabilities in addition (or instead) to the pan-tilt capabilities of the servos. This allows system 300 to adjust and modify the focal point of the optical system, optimize system 300 performances and energy throughput.

System 12 can communicate with system 20 which in some embodiments monitors the activity before, during and after system 300 projects the guided light source. System 20 can also automatically measure, quantify and analyze individual 18 or patient 16 responses to system 300, learn their behaviors and suggest certain type of alerts based on the observed behaviors.

More than one electromagnetic signaling system similar to system 300 can be employed with the same range detection system, and more than one range detection systems can be employed with the same electromagnetic signaling system.

Following are several examples for operation mode of system 300.

With the aid of system 300, individual 18 or patient 16 can interact with system 10 without any assistance from additional devices, such as 2D screen, and can see the location of the infected/contaminated points or surfaces on top of the real scene/object itself. Such capability is referred to as a Scene Contaminated Hologram.

Once system 10 detects that individual 18 enters the patient room and approach the patient without performing hand hygiene, system 300 can project a light beam onto the dispenser or onto the hands of individual 18. The light beam can signal individual 16 to execute hand hygiene activity. A similar procedure can be employed in connection to wearing or removal of gloves as further detailed hereinabove.

Once system 10 detects or predict a wrong hand touch (for instance, a contaminated hand touch or a hand touch without wearing a glove) at aseptic surface like a catheter or at operational wound, system 300 can project a light beam next to the expected or detected point of touch.

When more than one medical device signals individual 18, system 300 can project light beam according to a predetermined protocol to which of the devices the individual should approach before approaching other devices.

Elder people that suffer dementia and other memory difficulties may receive from system 300 automatic guidance for assisting them to follow their daily routine. By automatic monitoring the elder people activity and productivity as function of time, the system may provide diagnostic for the cognitive and physical condition of the elderly as well as may recommend different types of interventions.

System 300 may provide light beams at several colors in order to provide different messages, such as projection of red light beams with negative or warning messages, and green light beams with positive or rewarding messages. In addition, vocal text-to-speech digital commands may be added to the light signaling. System 300 may capture the attention of individual 18 and the additional vocal text-to-speech digital command may add explicit instructions and form improved communication capability with individual 18.

System 300 can also be used as a disinfection system, for example, by frequently projecting spatially focused disinfecting radiation, such as ultraviolet (UV) light, onto high risk areas (aseptic areas on patient body, surfaces expected to be contaminated). The disinfecting radiation can be projected automatically, for example, according to a predetermined protocol, or in response to a touch event identified, e.g., as further detailed hereinabove. The disinfecting radiation can be at a wavelength of from about 190 nm to about 300 nm or from about 250 nm to about 270 nm or from about 200 nm to about 215 nm or from about 190 nm to about 210 nm.

System 10 can automatically recognize touch events that involve contamination and evaluate contaminated environment next to the patient. Based on the events collected by system 10 a cost function can be obtained. In response to the cost function, system 300 can project or not project the disinfecting radiation onto a respective surface. The cost function can be calculated parameters, such as, but not limited to, the number of individuals that are in the close proximity to the patient, the distance between system 300 and the contaminated area, the distance between the contaminated area and the patient, the estimated level of contamination in the room or estimated contamination on a specific aseptic surface on patient body and the urgency of disinfection. System 10 can also calculate the illumination dose, duration and/or repetition rate based on the cost function.

In some embodiments of the present invention, a passive or active infrared marker, e.g., marker 26, are placed on top of specific objects or areas that are known as being frequently touched or contaminated by the staff or visitors, such as computer keyboard, door handles etc. These markers may optionally and preferably be coded differently than other infrared markers in the scene. The markers can be detected by system 12, and system 300 can direct the disinfection radiation to the surfaces on which the markers are placed more frequently than to other surfaces. When the marker is active it generates a signal that is detectable by system 12.

Some embodiments of the present invention provide a wound dressing that allows a range sensor to detect the aseptic area, and estimate its 3D location. Once the disinfecting radiation is focused and directed to the aseptic location, the wound dressing can protect the healthy tissue near the aseptic area in order to reduce radiation damage to healthy tissue.

Two examples of wound dressing assemblies are illustrated in FIGS. 10A and 10B. In FIGS. 10A and 10B, C is the contaminated area, B is a marker that is visible to system 12, preferably without violating patient privacy, and A is a transparent surface that allows the disinfecting radiation from system 300 to arrive the aseptic surface C and disinfect the aseptic surface. Region D is a surface that is non-transmissive the disinfecting radiation. For example, region D can be made of a material that absorbs the radiation. The radius of A and thickness or of B and D may be adjusted as a function of the healthy tissue dimensions and as a function of the diameter of the disinfecting radiation beam. For instance, for a wide disinfecting radiation beam and small infected aseptic area C, a smaller radius of A and a thicker wider D can be employed.

The marker B is optionally and preferably identifiable by system 12, as further detailed hereinabove. The marker can alternatively or additionally be coated with a material having a sufficiently high (e.g., higher than that of the object or individual being tagged by the marker) infrared reflectivity. These embodiments are particularly useful when system 12 employs active infrared illumination technique for generating the range data. Infrared reflective materials suitable for the present embodiments are disclosed in U.S. Pat. Nos. 3,711,176, 5,103,337, 6,174,360, in U.S. Published Application No. 20030215627, and in Ashwini K. Bendiganavale and Vinod C. Malshe, "Infrared Reflective Inorganic Pigments", Recent Patents on Chemical Engineering, 2008, 1, 67-79, and is commercially available from 3M™, USA. The marker can be mounted (e.g., attached) on the external surface of the respective object. Typically, but not necessarily, the marker is attached to the skin or clothing at the vicinity of a region having a high likelihood to contain infection, or a high likelihood to cause infectious disease once becoming infected. Such regions are typically near wound dressings, open wounds, near the entry points of minimally invasive medical devices into the body, and near natural openings of the body.

In some embodiments of the present invention the electromagnetic system 300 is employed to remotely heal patient wounds by remotely focusing and projecting a healing electromagnetic beam (infrared, blue light, sunlight, or any other electromagnetic radiation that can heal a wound) onto a contaminated surface. A wound dressing presented, such as the wound dressing shown in FIGS. 10A and 10B may be placed to indicate the exact location of the wound. System 300 may mix IR light (for healing and-or signaling) with UV light (for disinfection). It can be done by mixing waves with one or more of the optical elements illustrated in FIGS. 8A-H.

As used herein the term "about" refers to ±10%.

The word "exemplary" is used herein to mean "serving as an example, instance or illustration." Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments." Any particular embodiment of the invention may include a plurality of "optional" features unless such features conflict.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

[1] Clark, M. Wallace, and G. L. Pronzato, "Measuring range using a triangulation sensor with variable geometry," IEEE Trans. Rob. Autom. 14, 60-68 (1998).
[2] M. D. Adams, "Lidar Design, Use and Calibration Concepts for Correct Environmental Detection", IEEE Transactions on Robotics and Automation, Vol 16(6), December 2000.
[3] Kolb, E. Barth and R. Koch: "ToF-Sensors: New Dimensions for Realism and Interactivity," Proc. IEEE Comp. Soc. Conf. on Computer Vision and Pattern Recognition (CVPR), 1518-1523 (2008).
[4] M. Loh and P. D. Kovesi, "Estimation of surface normal of a curved surface using texture," In Proc. of the 7th Australian Pattern Recognition Society Conference—Digital Image Computing: Techniques and Applications, 155-164 (2003).
[5] David Catuhe "Programming with the Kinect for Windows Software Development Kit, Add gesture and posture recognition to your applications", Microsoft Press.
[6] R. C. Bolles, H. H. Baker, D. H. Marimont, "Epipolar-plane image analysis: An approach to determining structure from motion," International Journal of Computer Vision 1(1): 7-55 (1987).
[7] E. Trucco, A. Verri, "Introductory techniques for 3D computer vision," Prentice Hall, 140-143 (1998).
[8] Irshad Ali, 2009, "Detection and Tracking of Multiple Humans in High-Density Crowds". Thesis, Department of Computer Science Engineering, Asian Institute of Technology School of Engineering and Technology, Thailand.
[9] Bo Wu and Nevatia R., Detection of Multiple Partially Occluded Humans in a Single Image by Bayesian Combination of Edgelet Part Detectors. In 10th IEEE International Conference on Computer Vision, ICCV'05, Volume 1, Pages 90-97, 2005.
[10] Saad M. Khan and Mubarak Shah, A Multiview Approach to Tracking People in Crowded Scenes using a Planar Homography Constraint. In IEEE International Conference on Computer Vision, ECCV'06, Volume 3954, Pages 133-146, 2006.
[11] Cheriyadat, A. M., Bhaduri B. L. and Radke R. J., Detecting multiple moving objects in crowded environments with coherent motion regions. in IEEE Computer Society Conference, Pages: 1-8, 2008.
[12] Marchand E., Bouthemy P., Chaumette F. and Moreau V., Robust real-time visual tracking using a 2D-3D model-based approach. In Proc. Of the 7th IEEE International Conference on Computer Vision, ICCV'99, Volume 1, Pages 262-268, Kerkira, Greece, September 1999.
[13] Regazzoni, A. Cavallaro, Y. Wu, J. Konrad, A. Hampapur, Video Analytics for Surveillance: Theory and Practice, IEEE Signal Processing Magazine, September 2010.
[14] Fisher, J. 2003. "A Line Calling System to Improve Line Umpire Performance." In, ed. Stuart Miller. International Tennis Federation.
[15] U.S. Published Application No. 2010014781.
[16] U.S. Published Application No. 2011090318.
[17] International Publication No. 2012029058.
[18] Hosp Epidemiol Infect Control, 2nd Edition, 1999.
[19] Sax H, et al. 'My five moments for hand hygiene': a user-centred design approach to understand, train, monitor and report hand hygiene", J Hosp Infect 2007; 67(1): 9-21.
[20] U.S. Pat. No. 6,174,360.
[21] U.S. Published Application No. 20030215627.
[22] U.S. Pat. No. 5,103,337.
[23] U.S. Pat. No. 3,711,176.

What is claimed is:

1. A monitoring system, comprising:
a range detection system configured for scanning a scene to provide range data arranged gridwise over a plurality of picture elements which are devoid of any color data and any grayscale data, said range data including data describing range to a marker that is detectable by said range detection system and that is placed on a hand of an individual in said scene; and
a data processing system configured for processing said range data to identify said marker, to identify said hand based, at least in part on said range to said marker, to identify points of contact between said individual and objects in said scene, and to monitor hygienic activity of an individual in said scene.

2. The system according to claim 1, wherein said range detection system scans said scene from a single view point.

3. The system according to claim 1, wherein said range detection system provides range imaging data, and said data processing system is configured for removing from each picture-element any color data or grayscale data that allow identifying any individual in said scene.

4. The system according to claim 1, wherein said data processing system is configured to identify a medical treatment device in said scene, and contact events between said individual and said medical treatment device, and to determine a time window encompassing both said hygienic activity and said contact events.

5. The system according to claim 1, wherein said data processing system is configured to identify contact events between said individual and an organ of a patient in said scene, and to issue a notification when said contact events are not preceded or not followed by said hygienic activity.

6. The system according to claim 1, further comprising an electromagnetic signaling system configured to project a light beam on said individual or an object in said scene based on said hygienic activity or lack thereof.

7. The system according to claim 1, comprising an electromagnetic disinfecting system configured to project a disinfecting light beam on at least one of said points of contact.

8. A method of monitoring, comprising:

scanning a scene to provide range data to a marker that is placed on a hand of an individual in said scene, the range data being arranged gridwise over a plurality of picture elements which are devoid of any color data and any grayscale data; and processing said range data to identify said hand based, at least in part on said range to said marker, to identify points of contact between said individual and objects in said scene, and to monitor hygienic activity of an individual in said scene.

9. The method according to claim 8, wherein said scanning is from a single view point.

10. The method according to claim 8, further comprising identifying a medical treatment device in said scene and contact events between said individual and said medical treatment device, and determining a time window encompassing both said hygienic activity and said contact events.

11. The method according to claim 8, further comprising issuing a notification when said contact events are not preceded or not followed by said hygienic activity.

12. The method according to claim 8, further comprising projecting a light beam on said individual or an object in said scene based on said hygienic activity or lack thereof.

13. The method according to claim 8, further comprising projecting a disinfecting light beam on at least one of said points of contact.

14. A method of monitoring, comprising:

scanning a scene and provide range data including data describing a range to a hand of an individual in said scene and data describing a location of said individual within said scene, the range data being arranged gridwise over a plurality of picture elements which are devoid of any color data and any grayscale data; and correction said data describing said range to said hand based, at least in part on said data describing said location of said individual within said scene.

15. The method according to claim 14, further comprising processing said corrected data to monitor hygienic activity of an individual in said scene.

16. The method according to claim 14, further comprising determining at least one of a posture and an orientation of said individual, wherein said correction is based, at least in part, on at least one of said posture and orientation.

17. The method according to claim 14, further comprising identifying contact events between said individual and an organ of a patient in said scene, and issuing a notification when said contact events are not preceded or not followed by said hygienic activity.

18. The method according to claim 14, further comprising projecting a light beam on said individual or an object in said scene based on said hygienic activity or lack thereof.

19. The method according to claim 14, further comprising identifying points of contact between said individual and objects in said scene, and projecting a disinfecting light beam on at least one of said points of contact.

\* \* \* \* \*